(12) United States Patent
Amiji et al.

(10) Patent No.: US 9,173,840 B2
(45) Date of Patent: Nov. 3, 2015

(54) MULTIFUNCTIONAL SELF-ASSEMBLING POLYMERIC NANOSYSTEMS

(75) Inventors: Mansoor M. Amiji, Attleboro, MA (US); Arun K. Iyer, Boston, MA (US)

(73) Assignee: Northeastern University, Boston, MA (US)

(*) Notice: Subject to any disclaimer, the term of this patent is extended or adjusted under 35 U.S.C. 154(b) by 0 days.

(21) Appl. No.: 13/123,428

(22) PCT Filed: Oct. 9, 2009

(86) PCT No.: PCT/US2009/060175
§ 371 (c)(1),
(2), (4) Date: Jun. 15, 2011

(87) PCT Pub. No.: WO2010/042823
PCT Pub. Date: Apr. 15, 2010

(65) Prior Publication Data
US 2011/0244048 A1    Oct. 6, 2011

Related U.S. Application Data

(60) Provisional application No. 61/104,056, filed on Oct. 9, 2008, provisional application No. 61/246,355, filed on Sep. 28, 2009.

(51) Int. Cl.
*A61K 9/14* (2006.01)
*A61K 9/127* (2006.01)
*A61K 9/51* (2006.01)

(52) U.S. Cl.
CPC ............. *A61K 9/1273* (2013.01); *A61K 9/5161* (2013.01)

(58) Field of Classification Search
None
See application file for complete search history.

(56) References Cited

U.S. PATENT DOCUMENTS

| | | | |
|---|---|---|---|
| 4,708,930 A | 11/1987 | Kortright et al. | |
| 4,743,543 A | 5/1988 | Kortright | |
| 4,892,935 A | 1/1990 | Yoshida et al. | |
| 4,914,021 A | 4/1990 | Toth et al. | |
| 4,918,164 A | 4/1990 | Hellstrom et al. | |
| 4,921,789 A | 5/1990 | Salem et al. | |
| 4,921,790 A | 5/1990 | O'Brien | |
| 4,939,240 A | 7/1990 | Chu et al. | |
| 4,963,484 A | 10/1990 | Kufe | |
| 4,987,071 A | 1/1991 | Cech et al. | |
| 5,013,556 A | 5/1991 | Woodle et al. | |
| 5,053,489 A | 10/1991 | Kufe | |
| 5,110,911 A | 5/1992 | Samuel et al. | |
| 5,270,163 A | 12/1993 | Gold et al. | |
| 5,395,619 A | 3/1995 | Zalipsky et al. | |
| 5,475,096 A | 12/1995 | Gold et al. | |
| 5,512,443 A | 4/1996 | Schlom et al. | |
| 5,543,508 A | 8/1996 | Haseloff et al. | |
| 5,545,530 A | 8/1996 | Satomura et al. | |
| 5,567,588 A | 10/1996 | Gold et al. | |
| 5,580,737 A | 12/1996 | Polisky et al. | |
| 5,631,018 A | 5/1997 | Zalipsky et al. | |
| 5,660,985 A | 8/1997 | Pieken et al. | |
| 5,693,763 A | 12/1997 | Codington et al. | |
| 5,707,796 A | 1/1998 | Gold et al. | |
| 5,763,177 A | 6/1998 | Gold et al. | |
| 5,808,005 A | 9/1998 | Codington et al. | |
| 5,855,866 A | 1/1999 | Thorpe et al. | |
| 5,892,019 A | 4/1999 | Schlom et al. | |
| 5,892,020 A | 4/1999 | Mezes et al. | |
| 6,083,696 A | 7/2000 | Biesecker et al. | |
| 6,441,158 B1 | 8/2002 | Dynan et al. | |
| 6,458,559 B1 | 10/2002 | Shi et al. | |
| 6,586,001 B1 | 7/2003 | Zalipsky | |
| 2003/0077829 A1* | 4/2003 | MacLachlan | 435/458 |
| 2005/0077497 A1 | 4/2005 | Anderson | |
| 2006/0083781 A1* | 4/2006 | Shastri et al. | 424/450 |
| 2006/0222595 A1 | 10/2006 | Mukherjee et al. | |
| 2006/0240092 A1* | 10/2006 | Breitenkamp et al. | 424/450 |
| 2007/0048383 A1 | 3/2007 | Helmus | |
| 2008/0081074 A1* | 4/2008 | Gu et al. | 424/489 |
| 2008/0145432 A1 | 6/2008 | Kakizawa et al. | |

FOREIGN PATENT DOCUMENTS

| | | | |
|---|---|---|---|
| CA | WO2005007196 A2 * | 1/2005 | |
| WO | WO-2005007196 A2 | 1/2005 | |
| WO | WO-2007133807 A2 | 11/2007 | |
| WO | WO-2008105773 A2 | 9/2008 | |
| WO | WO-2008124632 A1 | 10/2008 | |

OTHER PUBLICATIONS

Bellamy, et al, "Multidrug resistance in the laboratory and clinic," Adv Clin Chem, vol. 31, pp. 1-61 (1994).

Bernstein, et al., "Higher antitumor efficacy of daunomycin when linked to dextran: in vivo and in vitro studies," J Natl Cancer Inst, vol. 60(2), pp. 379-384 (1978).

Berrada, et al, "Effect of a derivatized dextran on human osteoblast growth and phenotype expression," J Biomater Sci Polymer Ed, vol. 6(2), pp. 211-222 (1994).

Broxterman, et al., "Towards Functional Screening for Multidrug Resistant Cells in Human Malignancies," Pezcoller Foundation Symphosia1. Drug Resistance: Mechanisms and Reversal. Edited by Mihich E. Rome: John Libbey CIC; pp. 309-319, Total 12 pgs. (1990).

Chaudhary, et al., "Expression and activity of P-glycoprotein, a multidrug efflux pump, in human hematopoietic stem cells," Cell, vol. 66, pp. 85-94 (Jul. 12, 1991).

Chou, A.J. and Gorlick, R., "Chemotherapy resistance in osteosarcoma: current challenges and future directions," Expert Rev Anticancer Ther, vol. 6(7), pp. 1075-1085 (2006).

Dalgleish, A. G. et al., "The CD4 (T4) antigen is an essential component of the receptor for the AIDS retrovirus," Nature, vol. 312, pp. 763-767 (1984).

(Continued)

*Primary Examiner* — Jennifer McDonald

(74) *Attorney, Agent, or Firm* — Wilmer Cutler Pickering Hale and Dorr LLP

(57) ABSTRACT

Libraries of nanoparticles comprising therapeutic agents and/or imaging agents are disclosed, as well as methods of making, customizing, and using such libraries of nanoparticles.

15 Claims, 15 Drawing Sheets

(56) References Cited

OTHER PUBLICATIONS

Extended European Search Report issued by the European Patent Office for European Patent Application No. 09819950.8 dated Oct. 18, 2013 (14 pgs.).

Franssen, et al., "Enzymatic Degradation of Methacrylated Dextrans," Macromolecules, vol. 30, pp. 7408-7413 (1997).

Gottesman, et al., "Biochemistry of multidrug resistance mediated by the multidrug transporter," Annu Rev Biochem, vol. 62, pp. 385-427 (1993).

Horwitz, et al., "Taxol: mechanisms of action and resistance," J Natl Cancer Inst Monogr, vol. 15, pp. 55-61 (1993).

Hoste, et al., "Synthesis and characterization of poly(oxyethylene) modified dextrans," Macromol Rapid Commun, vol. 15, pp. 697-704 (1994).

International Search Report and Written Opinion issued by the U.S. Patent and Trademark Office as International Searching Authority for International Application No. PCT/US09/60175 mailed Jan. 26, 2010 (12 pgs.).

Jellinek et al., "Inhibition of receptor binding by high-affinity RNA ligands to vascular endothelial growth factor," Biochem, vol. 33, pp. 10450-10456 (1994).

Krishna, R. and Mayer, Lawrence D., "Multidrug resistance (MDR) in cancer. Mechanisms, reversal using modulators of MDR and the role of MDR modulators in influencing the pharmacokinetics of anticancer drugs," Eur J Pharm Sci, vol. 11, pp. 265-283 (2000).

Licht, et al., "P-glycoprotein-mediated multidrug resistance in normal and neoplastic hematopoietic cells," Ann Hematol, vol. 69, pp. 159-171 (1994).

Lukyanov, A. and Torchilin, V. P., "Micelles from lipid derivatives of water-soluble polymers as delivery systems for poorly soluble drugs," Adv Drug Deliv Rev, vol. 56, pp. 1273-1289 (2004).

Miettinen, et al., "Inhibition of P-glycoprotein-mediated docetaxel efflux sensitizes ovarian cancer cells to concomitant docetaxel and SN-38 exposure," Anti-Cancer Drugs, vol. 20, pp. 267-276 (2009).

Minko, et al. "Mechanisms of anticancer action of HPMA copolymer-bound doxorubicin," Macromol Symp, vol. 172, pp. 35-47 (2001).

Minko, et al., Chronic exposure to HPMA copolymer-bound adriamycin does not induce multidrug resistance in a human ovarian carcinoma cell line, J Control Release, vol. 59, pp. 133-148 (1999).

Takimoto, C. and Page, R., "Principles of chemotherapy." Cancer Management: A Multidisciplinary Approach: Medical, Surgical, and Radiation Oncology, 8th edition. Edited by Pazdur R. New York: PRP, pp. 21-38 (2004).

Sikic B.I., "Pharmacologic Approaches to Reversing Multidrug Resistance," Semin Hematol, vol. 34, pp. 40-47 (1997).

Sung et al., "Mechanical properties of a porcine aortic valve fixed with a naturally occurring crosslinking agent," Biomaterials, vol. 20, pp. 1759-1772 (1999).

Twentyman, et al., "Resistance modification by PSC-833, a novel non-immunosuppressive cyclosporin A," Eur J Cancer, vol. 27, No. 12, pp. 1639-1642 (1991).

Van Der Valk, et al., "Distribution of multi-drug resistance-associated p-glycoprotein in normal and neoplastic human tissues," Ann Oncol, vol. 1, pp. 56-64 (1990).

Van Vlerken, et al., "Poly (ethylene glycol)—modified Nanocarriers for Tumor-targeted and Intracellular Delivery," Pharmaceutical Research, vol. 24, No. 8, pp. 1405-1414 (2007).

Zalipsky, "Chemistry of polyethylene glycol conjugates with biologically active molecules," Adv. Drug. Del. Rev., vol. 16, pp. 157-182 (1995).

Zalipsky, et al, "Poly(ethylene glycol)—Grafted Liposomes with Oligopeptide or Oligosaccharide Ligands Appended to the Termini of the Polymer Chains," Bioconjug. Chem., vol. 8, pp. 111-118 (1997).

Zalipsky, et al., "Preparation of Poly(ethylene Glycol)—Grafted Liposomes with Ligands at the Extremities of Polymer Chains," Meth. Enzymol., vol. 387, pp. 50-69 (2004).

Zalipsky, et al., "Use of Functionalized Poly(Ethylene Glycol)s for Modification of Polypeptides," in Use of Polyethylene Glycol Chemistry, Biotechnical and Biomedical Applications, J.M. Harris, Ed., Plenum Press, New York, pp. 347-370 (1992).

Zhang, et al., "Synthesis and characterization of biodegradable network hydrogels having both hydrophobic and hydrophilic components with controlled swelling behavior," J. Polymer Science: Part A: Pol Chem, vol. 37, pp. 4554-4569 (1999).

\* cited by examiner

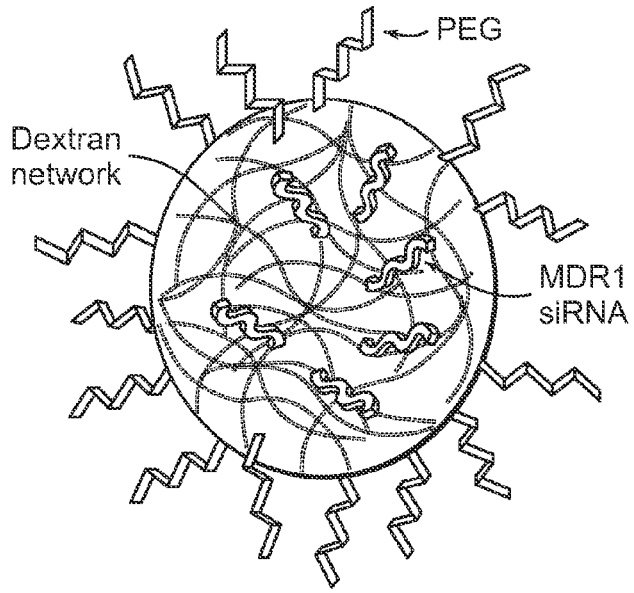
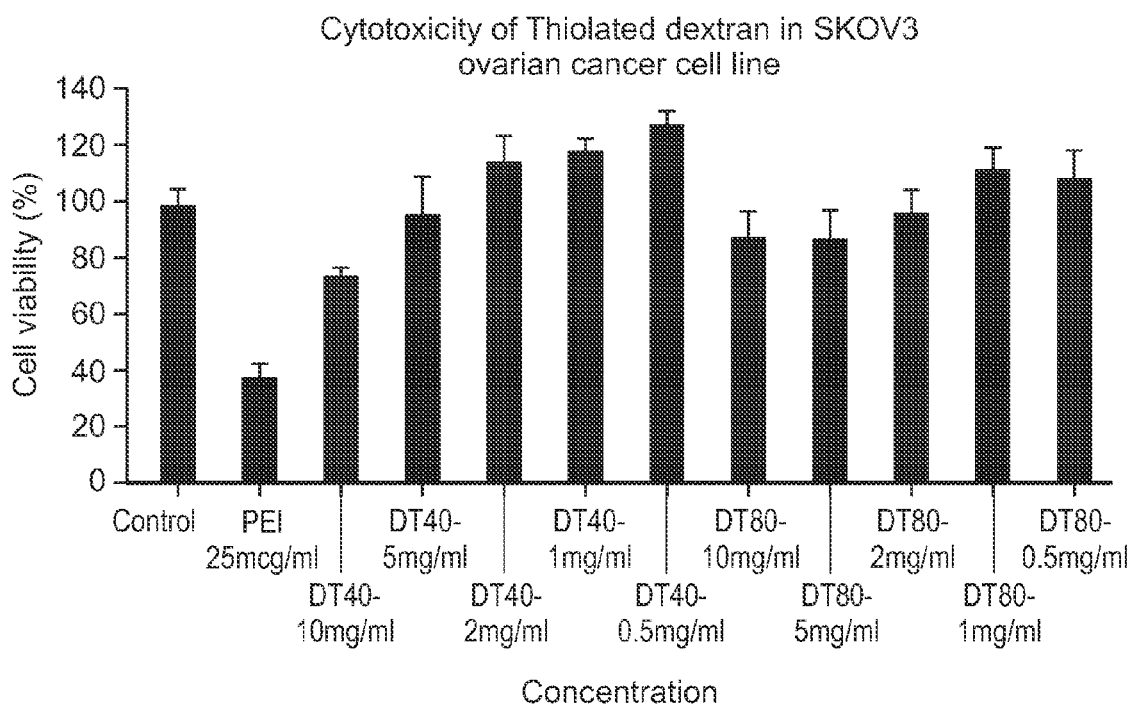
FIG. 7

SEQUENCE LISTING

```
<160> NUMBER OF SEQ ID NOS: 4

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gagcuuaaca cccgacuuau u                                              21

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
gaaaguauac cuccaguuuu u                                              21

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gaccauaaau guaagguuuu u                                              21

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
ccagguaugc cuauuauuau u                                              21
```

MULTIFUNCTIONAL SELF-ASSEMBLING POLYMERIC NANOSYSTEMS

CROSS REFERENCE TO RELATED APPLICATIONS

This application claims the benefit of priority of PCT Application No. US09/60175, filed Oct. 9, 2009, which claims the benefit of priority of U.S. Provisional Application No. 61/104,056, filed Oct. 9, 2008, and U.S. Provisional Application No. 61/246,355, filed Sep. 28, 2009, the entire contents of all of which are hereby incorporated by reference herein.

SEQUENCE LISTING

The instant application contains a Sequence Listing which has been submitted electronically in ASCII format and is hereby incorporated by reference in its entirety. Said ASCII copy, created on Mar. 25, 2014, is named 0067403.173US3_SL.txt and is 1,324 bytes in size.

FIELD OF THE INVENTION

The invention is in the field of therapeutic nanoparticles for medical treatment.

BACKGROUND

Delivery of nucleic acid therapies to specific disease tissue and cells in the body is challenging due to large molecular weight, negative charge, and relatively poor stability especially in biological fluids that are rich in degrading enzymes (such as DNAse and RNAse). Many technologies for nucleic acid delivery utilize cationic lipids and polymers that form electrostatic complexes (such as lipoplexes and polyplexes) with negatively-charged nucleic acid constructs. These cationic systems can be inefficient for gene therapy (with plasmid DNA) or RNA interference therapy (with siRNA) due to lack of intracellular release and stability. In addition, cationic lipids and polymers can be toxic to cells and tissues.

Drug resistance is a primary hindrance for the efficiency of chemotherapy against osteosarcoma. Although chemotherapy has improved the prognosis of osteosarcoma patients after introduction of neo-adjuvant therapy in the early 1980's, the outcome has since plateaued at approximately 70% for 5 year survival. The remaining 30% of the patients eventually develop resistance to multiple types of chemotherapy. There thus remains a need to overcome both the dose-limiting side effects of conventional chemotherapeutic agents and the therapeutic failure incurred from multidrug-resistant (MDR) tumor cells.

SUMMARY

The invention is based, at least in part, on the discovery of a modular platform of functional components for making customized libraries of nanoparticle formulations containing therapeutic and/or imaging agents. Accordingly, in one aspect, the invention features a method of making a customized nanoparticle library, the method comprising: a) determining the partition coefficient of a therapeutic agent; b) solubilizing the therapeutic agent in an aqueous solution; c) providing a first derivatized water-soluble polymer comprising PEG and a fatty acid; d) combining the solubilized therapeutic agent and the first water-soluble derivatized polymer, the solubilized therapeutic agent and the first water-soluble derivatized polymer self-assembling to form a first nanoparticle; e) providing a second derivatized water-soluble polymer comprising PEG and a fatty acid that differs from the fatty acid of the first derivatized water-soluble polymer; and f) repeating step d) to form a second nanoparticle, thereby making a customized nanoparticle library.

In some embodiments, the therapeutic agent has a partition coefficient greater than about 100, greater than about 200, greater than about 300, greater than about 400, greater than about 500, greater than about 600, greater than about 700, greater than about 800, greater than about 900, or greater than about 1000. In particular embodiments, the fatty acid is a $C_{14}$ fatty acid, a $C_{15}$ fatty acid, a $C_{16}$ fatty acid, a $C_{17}$ fatty acid, a $C_{18}$ fatty acid, a $C_{19}$ fatty acid, a $C_{20}$ fatty acid, a $C_{21}$ fatty acid, a $C_{22}$ fatty acid, a $C_{23}$ fatty acid, a $C_{24}$ fatty acid, a $C_{25}$ fatty acid, a $C_{26}$ fatty acid, a $C_{27}$ fatty acid, or a $C_{28}$ fatty acid.

In other embodiments, the therapeutic agent has a partition coefficient less than about 100, less than about 90, less than about 80, less than about 70, less than about 60, less than about 50, less than about 40, less than about 30, less than about 20, less than about 10, less than about 5, or less than about 1. In particular embodiments, the fatty acid is a $C_2$ fatty acid, a $C_3$ fatty acid, a $C_4$ fatty acid, a $C_5$ fatty acid, a $C_6$ fatty acid, a $C_7$ fatty acid, a $C_8$ fatty acid, a $C_9$ fatty acid, a $C_{10}$ fatty acid, a $C_{11}$ fatty acid, a $C_{12}$ fatty acid, a $C_{13}$ fatty acid, or a $C_{14}$ fatty acid.

In some embodiments, the first and the second water-soluble derivatized polymers form a hydrogel shell surrounding the solubilized therapeutic agent.

In other embodiments, the first and the second water-soluble derivatized polymers have a neutral charge. In particular embodiments, the first and the second water-soluble derivatized polymers are dextran, inulin, ficoll, starch, PEG, or poly(vinyl alcohol).

In yet other embodiments, the first and the second water-soluble derivatized polymers have a negative charge. In certain embodiments, the first and the second water-soluble derivatized polymers are alginate, hyaluronic acid, pectin, or a cellulose derivative.

In some embodiments, the method further comprising adding a crosslinking agent to the first and the second water-soluble derivatized polymers, thereby enhancing the stability of the nanoparticles. In certain embodiments, the crosslinking agent is a disulfide bond-forming crosslinking agent. In particular embodiments, the disulfide bond-forming crosslinking agent is cystamine, 2-immunothiolane, aminothiolane, glutathione, lipoic acid, glyoxal, or epichlorohydrin.

In other embodiments, the crosslinking agent is a divalent cation. In certain embodiments, the divalent cation is $Ca^{2+}$, $Mg^{2+}$, $Ba^{2+}$, or $Fe^{2+}$. In yet other embodiments, the crosslinking agent is a trivalent cation. In particular embodiments, the trivalent cation is $Al^{3+}$ or $Fe^{3+}$.

In yet other embodiments, the first and the second water-soluble derivatized polymers are modified with thiol groups. In other embodiments, the PEG is modified with thiol groups.

In certain embodiments, the PEG has a molecular weight of about 1,000 daltons, of about 1,500 daltons, of about 2,000 daltons, of about 2,500 daltons, of about 3,000 daltons, of about 3,500 daltons, of about 4,000 daltons, of about 4,500 daltons, of about 5,000 daltons, of about 6,000 daltons, of about 7,000 daltons, of about 8,000 daltons, of about 9,000 daltons, or of about 10,000 daltons.

In other embodiments, the PEG comprises a reactive group at one terminus. In certain embodiments, the reactive group is an acid, amine, maleimide, acrylate, or a succinimidyl carboxy methyl ester.

In yet other embodiments, the method further comprises linking a targeting agent to the reactive group on the PEG. In particular embodiments, the targeting agent is a nucleic acid, a polypeptide, a polysaccharide, or a small molecule. In particular embodiments, the targeting agent is folic acid, EGF, FGF, or an antibody to the tumor-associated antigens MUC 1, cMet receptor, or CD56 (NCAM).

In some embodiments, the therapeutic agent is a chemotherapeutic agent. In particular embodiments, the chemotherapeutic agent is doxorubicin, paclitaxel, or tamoxifen.

In yet other embodiments, the method further comprises conjugating the first and the second water-soluble polymers with diethylene triamine pentaacetic acid (DTPA). In particular embodiments, the method further comprises linking an imaging agent to the DTPA. In certain embodiments, the imaging agent is $^{64}$Gd, $^{111}$In, or $^{125}$I.

In some embodiments, the library comprises about 2, about 10, about 25, about 50, about 100, about 150, about 200, about 250, about 300, about 350, about 400, about 450, about 500, about 600, about 700, about 800, about 900, about 1,000, about 2,000, about 3,000, about 4,000, about 5,000, about 6,000, about 7,000, about 8,000, about 9,000, or about 10,000 different types of nanoparticles, or more.

In another aspect, the invention features a method of making a customized nanoparticle library, the method comprising: a) solubilizing a hydrophobic therapeutic agent in an aqueous solution; b) providing a first water-soluble derivatized polymer comprising polyethylene glycol (PEG) and a $C_{14}$-$C_{28}$ fatty acid; c) combining the solubilized therapeutic agent and the first derivatized polymer, the solubilized therapeutic agent and the first derivatized polymer self-assembling to form a first nanoparticle; d) providing a second water-soluble derivatized polymer comprising PEG and a $C_{14}$-$C_{28}$ fatty acid that differs from the fatty acid of the first derivatized polymer; and e) repeating step c) to form a second nanoparticle, thereby making a customized nanoparticle library.

In some embodiments, the therapeutic agent has a partition coefficient greater than about 100, greater than about 200, greater than about 300, greater than about 400, greater than about 500, greater than about 600, greater than about 700, greater than about 800, greater than about 900, or greater than about 1000.

In particular embodiments, the fatty acid is a $C_{14}$ fatty acid, a $C_{15}$ fatty acid, a $C_{16}$ fatty acid, a $C_r$ fatty acid, a $C_{18}$ fatty acid, a $C_{19}$ fatty acid, a $C_{20}$ fatty acid, a $C_{21}$ fatty acid, a $C_{22}$ fatty acid, a $C_{23}$ fatty acid, a $C_{24}$ fatty acid, a $C_{25}$ fatty acid, a $C_{26}$ fatty acid, a $C_{27}$ fatty acid, or a $C_{28}$ fatty acid.

In some embodiments, the first and the second water-soluble derivatized polymers form a hydrogel shell surrounding the solubilized therapeutic agent.

In other embodiments, the first and the second water-soluble derivatized polymers have a neutral charge. In particular embodiments, the first and the second water-soluble derivatized polymers are dextran, inulin, ficoll, starch, PEG, or poly(vinyl alcohol).

In yet other embodiments, the first and the second water-soluble derivatized polymers have a negative charge. In certain embodiments, the first and the second water-soluble derivatized polymers are alginate, hyaluronic acid, pectin, or a cellulose derivative.

In some embodiments, the method further comprising adding a crosslinking agent to the first and the second water-soluble derivatized polymers, thereby enhancing the stability of the nanoparticles. In certain embodiments, the crosslinking agent is a disulfide bond-forming crosslinking agent. In particular embodiments, the disulfide bond-forming crosslinking agent is cystamine, 2-immunothiolane, aminothiolane, glutathione, lipoic acid, glyoxal, or epichlorohydrin.

In other embodiments, the crosslinking agent is a divalent cation. In certain embodiments, the divalent cation is $Ca^{2+}$, $Mg^{2+}$, $Ba^{2+}$, or $Fe^{2+}$. In yet other embodiments, the crosslinking agent is a trivalent cation. In particular embodiments, the trivalent cation is $Al^{3+}$ or $Fe^{3+}$.

In yet other embodiments, the first and the second water-soluble derivatized polymers are modified with thiol groups. In other embodiments, the PEG is modified with thiol groups.

In certain embodiments, the PEG has a molecular weight of about 1,000 daltons, of about 1,500 daltons, of about 2,000 daltons, of about 2,500 daltons, of about 3,000 daltons, of about 3,500 daltons, of about 4,000 daltons, of about 4,500 daltons, of about 5,000 daltons, of about 6,000 daltons, of about 7,000 daltons, of about 8,000 daltons, of about 9,000 daltons, or of about 10,000 daltons.

In other embodiments, the PEG comprises a reactive group at one terminus. In certain embodiments, the reactive group is an acid, amine, maleimide, acrylate, or a succinimidyl carboxy methyl ester.

In yet other embodiments, the method further comprises linking a targeting agent to the reactive group on the PEG. In particular embodiments, the targeting agent is a nucleic acid, a polypeptide, a polysaccharide, or a small molecule. In particular embodiments, the targeting agent is folic acid, EGF, FGF, or an antibody to the tumor-associated antigens MUC 1, cMet receptor, or CD56 (NCAM).

In some embodiments, the therapeutic agent is a chemotherapeutic agent. In particular embodiments, the chemotherapeutic agent is doxorubicin, paclitaxel, or tamoxifen.

In yet other embodiments, the method further comprises conjugating the first and the second water-soluble polymers with diethylene triamine pentaacetic acid (DTPA). In particular embodiments, the method further comprises linking an imaging agent to the DTPA. In certain embodiments, the imaging agent is $^{64}$Gd, $^{111}$In, or $^{125}$I.

In some embodiments, the library comprises about 2, about 10, about 25, about 50, about 100, about 150, about 200, about 250, about 300, about 350, about 400, about 450, about 500, about 600, about 700, about 800, about 900, about 1,000, about 2,000, about 3,000, about 4,000, about 5,000, about 6,000, about 7,000, about 8,000, about 9,000, or about 10,000 different types of nanoparticles, or more.

In another aspect, the invention features a method of making a customized nanoparticle library, the method comprising: a) solubilizing a hydrophilic therapeutic agent in an aqueous solution; b) providing a first water-soluble derivatized polymer comprising polyethylene glycol (PEG) and a $C_2$-$C_{14}$ fatty acid; c) combining the solubilized therapeutic agent and the first derivatized polymer, the solubilized therapeutic agent and the first derivatized polymer self-assembling to form a first nanoparticle; d) providing a second water-soluble derivatized polymer comprising PEG and a $C_2$-$C_{14}$ fatty acid that differs from the fatty acid of the first derivatized polymer; and e) repeating step c) to form a second nanoparticle, thereby making a customized nanoparticle library.

In other embodiments, the therapeutic agent has a partition coefficient less than about 100, less than about 90, less than about 80, less than about 70, less than about 60, less than about 50, less than about 40, less than about 30, less than about 20, less than about 10, less than about 5, or less than about 1.

In particular embodiments, the fatty acid is a $C_2$ fatty acid, a $C_3$ fatty acid, a $C_4$ fatty acid, a $C_5$ fatty acid, a $C_6$ fatty acid, a $C_7$ fatty acid, a $C_8$ fatty acid, a $C_9$ fatty acid, a $C_{10}$ fatty acid, a $C_{11}$ fatty acid, a $C_{12}$ fatty acid, a $C_{13}$ fatty acid, or a $C_{14}$ fatty acid.

In some embodiments, the first and the second water-soluble derivatized polymers form a hydrogel shell surrounding the solubilized therapeutic agent.

In other embodiments, the first and the second water-soluble derivatized polymers have a neutral charge. In particular embodiments, the first and the second water-soluble derivatized polymers are dextran, inulin, ficoll, starch, PEG, or poly(vinyl alcohol).

In yet other embodiments, the first and the second water-soluble derivatized polymers have a negative charge. In certain embodiments, the first and the second water-soluble derivatized polymers are alginate, hyaluronic acid, pectin, or a cellulose derivative.

In some embodiments, the method further comprising adding a crosslinking agent to the first and the second water-soluble derivatized polymers, thereby enhancing the stability of the nanoparticles. In certain embodiments, the crosslinking agent is a disulfide bond-forming crosslinking agent. In particular embodiments, the disulfide bond-forming crosslinking agent is cystamine, 2-immunothiolane, aminothiolane, glutathione, lipoic acid, glyoxal, or epichlorohydrin.

In other embodiments, the crosslinking agent is a divalent cation. In certain embodiments, the divalent cation is $Ca^{2+}$, $Mg^{2+}$, $Ba^{2+}$, or $Fe^{2+}$. In yet other embodiments, the crosslinking agent is a trivalent cation. In particular embodiments, the trivalent cation is $Al^{3+}$ or $Fe^{3+}$.

In yet other embodiments, the first and the second water-soluble derivatized polymers are modified with thiol groups. In other embodiments, the PEG is modified with thiol groups.

In certain embodiments, the PEG has a molecular weight of about 1,000 daltons, of about 1,500 daltons, of about 2,000 daltons, of about 2,500 daltons, of about 3,000 daltons, of about 3,500 daltons, of about 4,000 daltons, of about 4,500 daltons, of about 5,000 daltons, of about 6,000 daltons, of about 7,000 daltons, of about 8,000 daltons, of about 9,000 daltons, or of about 10,000 daltons.

In other embodiments, the PEG comprises a reactive group at one terminus. In certain embodiments, the reactive group is an acid, amine, maleimide, acrylate, or a succinimidyl carboxy methyl ester.

In yet other embodiments, the method further comprises linking a targeting agent to the reactive group on the PEG. In particular embodiments, the targeting agent is a nucleic acid, a polypeptide, a polysaccharide, or a small molecule. In particular embodiments, the targeting agent is folic acid, EGF, FGF, or an antibody to the tumor-associated antigens MUC 1, cMet receptor, or CD56 (NCAM).

In some embodiments, the therapeutic agent is a nucleic acid. In particular embodiments, the nucleic acid is an siRNA molecule, an aptamer, or a ribozyme.

In yet other embodiments, the method further comprises conjugating the first and the second water-soluble polymers with diethylene triamine pentaacetic acid (DTPA). In particular embodiments, the method further comprises linking an imaging agent to the DTPA. In certain embodiments, the imaging agent is $^{64}Gd$, $^{111}In$, or $^{125}I$.

In some embodiments, the library comprises about 2, about 10, about 25, about 50, about 100, about 150, about 200, about 250, about 300, about 350, about 400, about 450, about 500, about 600, about 700, about 800, about 900, about 1,000, about 2,000, about 3,000, about 4,000, about 5,000, about 6,000, about 7,000, about 8,000, about 9,000, or about 10,000 different types of nanoparticles, or more.

In another aspect, the invention features a method of making a customized nanoparticle library, the method comprising: a) providing a first water-soluble derivatized polymer comprising (i) PEG, (ii) DTPA, and (iii) a $C_{14}$-$C_{28}$ fatty acid; b) combining an imaging agent and the first derivatized polymer, the imaging agent and the first derivatized polymer self-assembling to form a first nanoparticle; c) providing a second water-soluble derivatized polymer comprising (i) PEG, (ii) DTPA, and (iii) a $C_{14}$-$C_{28}$ fatty acid that differs from the fatty acid of the first derivatized polymer; and d) repeating step b) to form a second nanoparticle, thereby making a customized nanoparticle library.

In some embodiments, the imaging agent is $^{64}Gd$, $^{111}In$, or $^{125}I$. In other embodiments, the first and second water-soluble derivatized polymers, the PEG, and the $C_{14}$-$C_{28}$ fatty acids are any described herein.

In another aspect, the invention features a method of making a customized nanoparticle library, the method comprising: a) providing a first derivatized polymer comprising (i) PEG, (ii) DTPA, and (iii) a $C_2$-$C_{14}$ fatty acid; b) combining an imaging agent and the first derivatized polymer, the imaging agent and the first derivatized polymer self-assembling to form a first nanoparticle; d) providing a second derivatized polymer comprising (i) PEG, (ii) DTPA, and (iii) a $C_2$-$C_{14}$ fatty acid that differs from the fatty acid of the first derivatized polymer; and e) repeating step c) to form a second nanoparticle, thereby making a customized nanoparticle library.

In some embodiments, the imaging agent is iron oxide or a quantum dot. In other embodiments, the first and second water-soluble derivatized polymers, the PEG, and the $C_2$-$C_{14}$ fatty acids are any described herein.

In another aspect, the invention features a method of treating a subject having a tumor, the method comprising administering to the subject a nanoparticle in an amount sufficient to reduce tumor size or number of tumor cells in the tumor, wherein the nanoparticle comprises: a) a therapeutic agent; b) a hydrogel shell surrounding the therapeutic agent, the hydrogel shell comprising a water-soluble derivatized polymer comprising (i) a $C_{14}$-$C_{28}$ fatty acid, (ii), PEG, and (iii) a crosslinking agent; and c) a targeting agent bound to the PEG, thereby treating the subject.

In some embodiments, the water-soluble derivatized polymer is dextran, inulin, ficoll, starch, PEG, or poly(vinyl alcohol). In particular embodiments, the water-soluble derivatized polymer is dextran. In certain embodiments, the water-soluble derivatized polymer comprises thiolated dextran.

In other embodiments, the fatty acid is a $C_{16}$, a $C_{18}$, or a $C_{20}$ fatty acid.

In some embodiments, the subject is a vertebrate. In certain embodiments, the subject is a mammal. In particular embodiments, the subject is a human.

In yet another aspect, the invention features a method of inhibiting expression of a target polypeptide in a subject, the method comprising administering to the subject a nanoparticle in an amount sufficient to inhibit expression of the target polypeptide, wherein the nanoparticle comprises: a) an siRNA molecule; b) a hydrogel shell surrounding the siRNA molecule, the hydrogel shell comprising a water-soluble derivatized polymer comprising (i) a $C_2$-$C_{14}$ fatty acid, (ii), PEG, and (iii) a crosslinking agent; and c) a targeting agent bound to the PEG, thereby inhibiting the expression of the target polypeptide.

In some embodiments, the water-soluble derivatized polymer is dextran, inulin, ficoll, starch, PEG, or poly(vinyl alcohol). In particular embodiments, the water-soluble derivatized polymer is dextran. In certain embodiments, the water-soluble derivatized polymer comprises thiolated dextran.

In some embodiments, the subject is a vertebrate. In certain embodiments, the subject is a mammal. In particular embodiments, the subject is a human.

In yet another aspect, the invention features a nanoparticle library produced by any of the methods described herein. In some embodiments, the library comprises about 2, about 10, about 25, about 50, about 100, about 150, about 200, about 250, about 300, about 350, about 400, about 450, about 500, about 600, about 700, about 800, about 900, about 1,000, about 2,000, about 3,000, about 4,000, about 5,000, about 6,000, about 7,000, about 8,000, about 9,000, or about 10,000 different types of nanoparticles, or more.

In another aspect, the invention features the use of a nanoparticle described herein in the manufacture of a medicament to treat a disorder described herein. In some embodiments, the medicament includes additional therapeutic agents for the treatment of a disorder.

DEFINITIONS

As used herein, "about" means a numeric value having a range of ±10% around the cited value.

As used herein, a "subject" is a mammal, e.g., a human, mouse, rat, guinea pig, dog, cat, horse, cow, pig, or non-human primate, such as a monkey, chimpanzee, baboon or rhesus.

As used herein, the term "biodegradable" refers to a substance that is decomposed (e.g., chemically or enzymatically) or broken down in component molecules by natural biological processes (e.g., in vertebrate animals such as humans).

As used herein, the term "biocompatible" refers to a substance that has no unintended toxic or injurious effects on biological functions in a target organism.

As used herein, the term "nanoparticle" refers to a particle having a diameter in the range of about 50 nm to about 1000 nm. Nanoparticles include particles capable of containing a therapeutic or imaging agent that can be released within a subject.

As used herein, the terms "conjugated", "derivatized", and "linked" are used interchangeably, and mean that two components are physically linked by, for example, covalent chemical bonds or physical forces such van der Waals or hydrophobic interactions. Two components can also be conjugated indirectly, e.g., through a linker, such as a chain of covalently linked atoms.

As used herein, "treat," "treating" or "treatment" refers to administering a therapy in an amount, manner (e.g., schedule of administration), and/or mode (e.g., route of administration), effective to improve a disorder (e.g., a disorder described herein) or a symptom thereof, or to prevent or slow the progression of a disorder (e.g., a disorder described herein) or a symptom thereof. This can be evidenced by, e.g., an improvement in a parameter associated with a disorder or a symptom thereof, e.g., to a statistically significant degree or to a degree detectable to one skilled in the art. An effective amount, manner, or mode can vary depending on the subject and may be tailored to the subject. By preventing or slowing progression of a disorder or a symptom thereof, a treatment can prevent or slow deterioration resulting from a disorder or a symptom thereof in an affected or diagnosed subject.

An "effective amount", when used in connection with a composition described herein, is an amount effective for treating a disorder or a symptom thereof.

The term "polymer," as used herein, refers to a molecule composed of repeated subunits. Such molecules include, but are not limited to, polypeptides, polynucleotides, polysaccharides or polyalkylene glycols. Polymers can also be biodegradable and/or biocompatible.

The terms "polypeptide," "peptide," and "protein" are used interchangeably herein and refer to a polymer of amino acid residues. The terms apply to naturally occurring amino acid polymers as well as amino acid polymers in which one or more amino acid residues are non-natural amino acids. Additionally, such polypeptides, peptides, and proteins include amino acid chains of any length, including full length proteins, wherein the amino acid residues are linked by covalent peptide bonds.

The term "drug" or "therapeutic agent," as used herein, refers to any substance used in the prevention, diagnosis, alleviation, treatment, or cure of a disease or condition.

The term "targeting agent" refers to a ligand or molecule capable of specifically or selectively (i.e., non-randomly) binding or hybridizing to, or otherwise interacting with, a desired target molecule. Examples of targeting agents include, but are not limited to, nucleic acid molecules (e.g., RNA and DNA, including ligand-binding RNA molecules such as aptamers, antisense, or ribozymes), polypeptides (e.g., antigen binding proteins, receptor ligands, signal peptides, and hydrophobic membrane spanning domains), antibodies (and portions thereof), organic molecules (e.g., biotin, carbohydrates, and glycoproteins), and inorganic molecules (e.g., vitamins). A nanoparticle described herein can have affixed thereto one or more of a variety of such targeting agents.

As used herein, "self assembly", "self-assembled", or "self-assembling" means that components assemble into a nanoparticle without the application of a physical force, such as sonication, high pressure, membrane intrusion, or centrifugation.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 6 is a schematic illustration of MDR1 siRNA-loaded stearylamine-dextran modified nanoparticles.

FIG. 7 is a graphic representation of cytotoxicity of thiolated dextran in SKOV3 cells.

DETAILED DESCRIPTION

All publications, patent applications, patents, and other references mentioned herein, including GenBank database sequences, are incorporated by reference in their entirety. Unless otherwise defined, all technical and scientific terms used herein have the same meaning as commonly understood by one of ordinary skill in the art to which this invention belongs. In case of conflict, the present specification, including definitions, will control. In addition, the materials, methods, and examples are illustrative only and not intended to be limiting. Although methods and materials similar or equivalent to those described herein can be used in the practice or testing of the present invention, suitable methods and materials are described below.

Other features and advantages of the invention will be apparent from the following detailed description, and from the claims.

Figure 1:
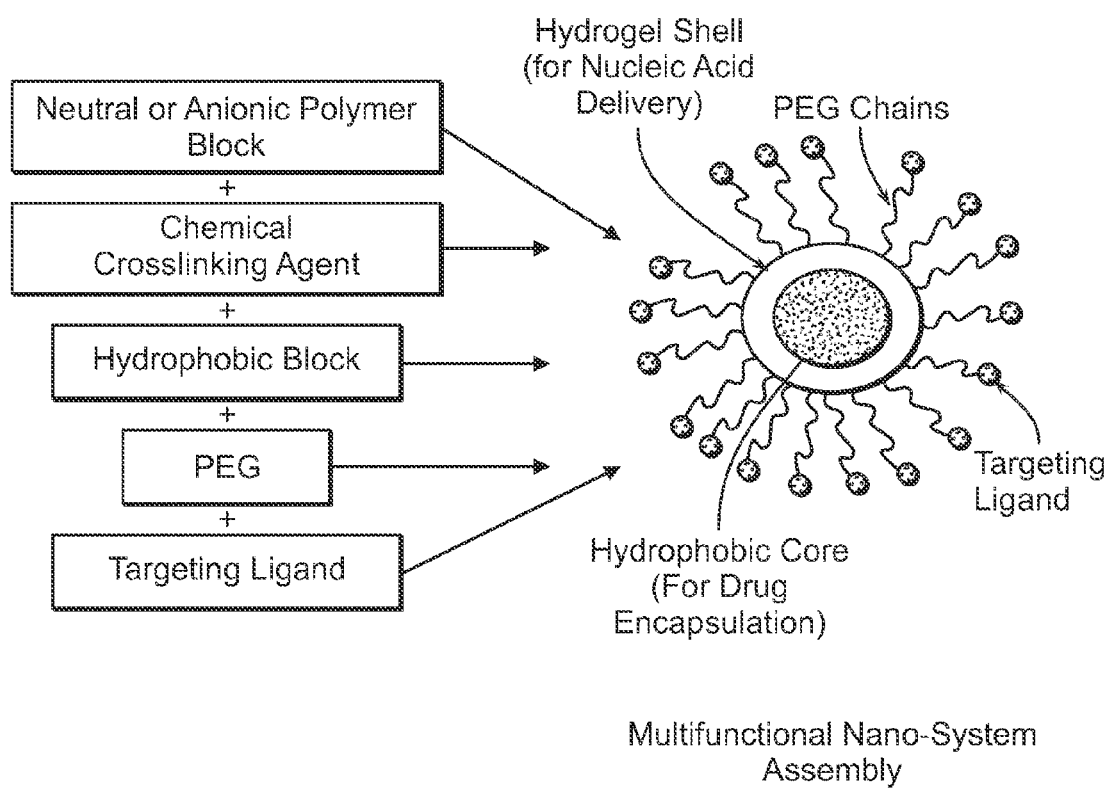
FIG. 1 is a schematic illustration of a multifunctional polymer library.

The present disclosure relates to the preparation and customization of multifunctional, polymeric nano-systems useful for facilitating delivery of therapeutic agents and/or imaging agents to tissues and cells, such as diseased tissues and cells. One exemplary polymeric nano-system is depicted schematically in FIG. 1. As shown in FIG. 1, a nanoparticle library can be synthesized using a combinatorial chemical approach based on at least three of the following functional components: a polymer, a hydrophobic or hydrophilic agent (lipid), polyethylene glycol (PEG), a crosslinking agent, and a targeting agent. In some instances, at least three of these components are used to prepare the nanoparticle: a polymer, a hydrophobic or hydrophilic agent, and PEG. In other instances, all five components are used. As described herein, the particular components and their arrangement are selected based on physicochemical properties of the therapeutic agents and/or imaging agents to be delivered.

Polymers

The nanoparticles described herein include water-soluble polymers, such as neutral or anionic water-soluble polymers. Such polymers include, without limitation, poly(styrene-sulfonate), polyglutamic or alginic acids, poly(acrylic acid), poly(aspartic acid), poly(glutaric acid), and natural polyelectrolytes with similar ionized groups such as dextran sulfate, carboxymethyl cellulose, hyaluronic acid, sodium alginate, gelatine B, chondroitin sulfate, and/or heparin. These polymers can be synthesized, isolated, or commercially obtained. In some instances, the polymer is a homopolymer or a copolymer.

In certain instances, neutral or negatively-charged water-soluble biodegradable and/or biocompatible polymers are used. These include, without limitation, substantially pure carbon lattices (e.g., graphite), dextran, polysaccharides, polypeptides, polynucleotides, acrylate gels, polyanhydride, poly(lactide-co-glycolide), polytetrafluoroethylene, polyhydroxyalkonates, cross-linked alginates, gelatin, collagen, cross-linked collagen, collagen derivatives (such as succinylated collagen or methylated collagen), cross-linked hyaluronic acid, chitosan, chitosan derivatives (such as methylpyrrolidone-chitosan), cellulose and cellulose derivatives (such as cellulose acetate or carboxymethyl cellulose), dextran derivatives (such carboxymethyl dextran), starch and derivatives of starch (such as hydroxyethyl starch), other glycosaminoglycans and their derivatives, other polyanionic polysaccharides or their derivatives, polylactic acid (PLA), polyglycolic acid (PGA), a copolymer of a polylactic acid and a polyglycolic acid (PLGA), lactides, glycolides, and other polyesters, polyglycolide homoploymers, polyoxanones and polyoxalates, copolymer of poly(bis(p-carboxyphenoxy)propane)anhydride (PCPP) and sebacic acid, poly(l-glutamic acid), poly(d-glutamic acid), polyacrylic acid, poly(dl-glutamic acid), poly(l-aspartic acid), poly(d-aspartic acid), poly(dl-aspartic acid), polyethylene glycol, copolymers of the above listed polyamino acids with polyethylene glycol, polypeptides, such as, collagen-like, silk-like, and silk-elastin-like proteins, polycaprolactone, poly(alkylene succinates), poly(hydroxy butyrate) (PHB), poly(butylene diglycolate), nylon-2/nylon-6-copolyamides, polydihydropyrans, polyphosphazenes, poly(ortho ester), poly(cyano acrylates), polyvinylpyrrolidone, polyvinylalcohol, poly casein, keratin, myosin, and fibrin, silicone rubbers, or polyurethanes, and the like. Other neutral or negatively-charged water-soluble polymers that can be used include naturally derived polymers, such as acacia, gelatin, dextrans, albumins, alginates/starch, and the like; or synthetic polymers, whether hydrophilic or hydrophobic. The materials can be synthesized, isolated, and are commercially available.

Particular nonlimiting examples of polymers that can be used in the methods and compositions described herein include dextran, inulin, ficoll, water-soluble starch, alginate, cellulose derivatives, poly(vinyl alcohol), mono- and disaccharides and derivatives, acrylate derivatives, and ethylene glycol.

Hydrophobic and Hydrophilic Agents

As depicted in FIG. 1, a nanoparticle described herein can include a hydrophobic therapeutic agent or a hydrophobic imaging agent. In such instances, the nanoparticle can include a fatty acid or fatty acid derivative, such as a $C_{14}$ to a $C_{28}$ fatty acid. Nonlimiting examples of hydrophobic agents include stearic acid, stearylamine, oleic acid, oleylamine, palmitic acid, laurylamine, dodecylamine, poly(propylene glycol-methyl ether acrylate, neopentyl glycol methyl ether propoxylate, polycaprolactone-diol (PCL), and polylactic glycolic acid-diol (PLGA).

In other instances, such as when a therapeutic agent or imaging agent to be delivered is hydrophilic, the nanoparticle can include a fatty acid or fatty acid derivative, such as a $C_2$ to a $C_{14}$ fatty acid. Nonlimiting examples of hydrophilic agents include acetic acid, propionic acid, butyric acid, valeric acid, hexanoic acid, and octanoic acid.

A water-soluble polymer described herein can be derivatized or conjugated with a hydrophobic agent, e.g., a $C_2$ to a $C_{28}$ fatty acid. A polymer can be conjugated to a fatty acid using known methods, for example, as described in Zalipsky et al., *Bioconjug. Chem.* 8:111 (1997); Zalipsky et al., *Meth. Enzymol.* 387:50 (2004); U.S. Pat. No. 5,631,018; U.S. Pat. No. 5,395,619; U.S. Pat. No. 6,586,001; and U.S. Pat. No. 5,013,556.

In particular instances, a nanoparticle library described herein includes polymers having varying degrees of fatty acid saturation. For example, about 10% of the polymers can be conjugated with fatty acids, about 20%, about 30%, about 40%, about 50%, about 60%, about 70%, about 80%, about 90%, or about 100% of the polymers can be conjugated with fatty acids.

Crosslinking Agents

As depicted in FIG. 1, another functional component that can be included in a nanoparticle described herein includes a crosslinking agent. The crosslinking agent can react with the water-soluble polymers to form crosslinked hydrogels and interpenetrating networks (IPN). Any crosslinking agent known to crosslink any of the polymers described herein can be used.

Nonlimiting examples of crosslinking agents include reagents that form disulfide bonds (e.g., aminothiolane, cystamine, glutathione, 2-immunothiolane, and lipoic acid) and other covalent crosslinkers such as glyoxal, epichlorohydrin. Without wishing to be bound by theory, it is believed that intermolecular disulfide crosslinking of thiol-modified polymers can yield nanoparticles that have enhanced stability, such as in the circulatory system, but that can dissociate in a highly reduced environment, such as the environment of a tumor cell. In some situations, a covalent disulfide crosslinking can enhance intracellular delivery and overcome efflux of a therapeutic agent by preventing premature release of the therapeutic agent, such as in an endosomal/lysosomal compartment.

Other nonlimiting examples of crosslinkers include cations. In some instances, divalent cations such as $Ca^{2+}$, $Mg^{2+}$, $Ba^{2+}$, or $Fe^{2+}$ are used. In other situations, trivalent cations such as $Al^{3+}$ or $Fe^{3+}$ are used.

Other crosslinking agents that can be used in the methods and compositions described herein include, e.g., genipin (Biomaterials 20:1759-72, 1999), epoxy compounds, dialdehyde starch, glutaraldehyde, formaldehyde, dimethyl suberimidate, carbodiimides, succinimidyls, diisocyanates, acyl azide, reuterin, ultraviolet irradiation, dehydrothermal treatment, tris(hydroxymethyl)phosphine, ascorbate-copper, glucose-lysine and photo-oxidizers.

Polyethylene Glycol

As depicted in FIG. 1, a nanoparticle described herein can include polyethylene glycol (PEG). Nonlimiting examples of PEG that can be used in the methods and compositions described herein include PEGs having a molecular weight of about 1,000 to about 10,000 daltons.

In some instances, a PEG is coupled to a targeting agent described herein. To couple PEG to a targeting agent, the PEG can be activated by preparing a derivative of the PEG having a reactive group at one terminus. Many activated derivatives of PEG are known in the art. One nonlimiting example of an activated PEG derivative is the succinimidyl succinate ester of PEG (see, e.g., U.S. Pat. No. 4,179,337). Other nonlimiting examples of activated PEG molecules that can be used in the methods described herein include PEGs having a reactive cyanuric chloride moiety, succinimidyl carbonates of PEG, phenylcarbonates of PEG, imidazolyl formate derivatives of PEG, PEG-carboxymethyl azide, PEG-imidoesters, PEG-vinyl sulfone, active ethyl sulfone derivatives of PEG, tresylates of PEG, PEG-phenylglyoxal, PEGs activated with an aldehyde group, PEG-maleimides, and PEGs with a terminal amino moiety. These PEG derivatives and methods for conjugating such derivatives to agents are known in the art (see, e.g., Zalipsky et al., "Use of Functionalized Poly(Ethylene Glycol)s for Modification of Polypeptides", in *Use of Polyethylene Glycol Chemistry. Biotechnical and Biomedical Applications*, J. M. Harris, Ed., Plenum Press, New York (1992); see also Zalipsky, *Adv. Drug Rev.* 16:157-182 (1995)).

Targeting Agents

The final component depicted in FIG. 1 consists of a targeting agent, which is linked to a PEG as described herein. In certain situations, the targeting agent specifically binds to a particular biological target. Nonlimiting examples of biological targets include tumor cells, bacteria, viruses, cell surface proteins, cell surface receptors, cell surface polysaccharides, extracellular matrix proteins, intracellular proteins and intracellular nucleic acids. The targeting agents can be, for example, various specific ligands, such as antibodies, monoclonal antibodies and their fragments, folate, mannose, galactose and other mono-, di-, and oligosaccharides, and RGD peptide.

The nanoparticles and methods described herein are not limited to any particular targeting agent, and a variety of targeting agents can be used. Examples of such targeting agents include, but are not limited to, nucleic acids (e.g., RNA and DNA), polypeptides (e.g., receptor ligands, signal peptides, avidin, Protein A, and antigen binding proteins), polysaccharides, biotin, hydrophobic groups, hydrophilic groups, drugs, and any organic molecules that bind to receptors. In some instances, a nanoparticle described herein can be conjugated to one, two, or more of a variety of targeting agents. For example, when two or more targeting agents are used, the targeting agents can be similar or dissimilar. Utilization of more than one targeting agent in a particular nanoparticle can allow the targeting of multiple biological targets or can increase the affinity for a particular target.

The targeting agents can be associated with the nanoparticles in a number of ways. For example, the targeting agents can be associated (e.g., covalently or noncovalently bound) to other subcomponents/elements of the nanoparticle with either short (e.g., direct coupling), medium (e.g., using small-molecule bifunctional linkers such as SPDP (Pierce Biotechnology, Inc., Rockford, Ill.)), or long (e.g., PEG bifunctional linkers (Nektar Therapeutics, Inc., San Carlos, Calif.)) linkages. Alternatively, such agents can be directly conjugated to the outermost polymeric layer.

In addition, polymers used to produce the nanoparticles described herein can also incorporate reactive groups (e.g., amine groups such as polylysine, dextranemine, profamine sulfate, and/or chitosan). The reactive group can allow for further attachment of various specific ligands or reporter groups (e.g., $^{125}$I, $^{131}$I, I, Br, various chelating groups such as DTPA, which can be loaded with reporter heavy metals such as $^{111}$In, 99m-Tc, GD, Mn, fluorescent groups such as FITC, rhodamine, Alexa, and quantum dots), and/or other moieties (e.g., ligands, antibodies, and/or portions thereof). These moieties can also be incorporated into the polymeric shell during its formation of a nanoparticle described herein.

Antibodies as Targeting Agents

In some instances, the targeting agents are antigen binding proteins or antibodies or antigen-specific binding portions thereof. Antibodies can be generated to allow for the specific targeting of antigens or immunogens (e.g., tumor, tissue, or pathogen specific antigens) on various biological targets (e.g., pathogens, tumor cells, normal tissue). Such antibodies include, but are not limited to, polyclonal antibodies; monoclonal antibodies or antigen binding fragments thereof; modified antibodies such as chimeric antibodies, reshaped antibodies, humanized antibodies, or fragments thereof (e.g., Fv, Fab', Fab, F(ab')$_2$); or biosynthetic antibodies, e.g., single chain antibodies, single domain antibodies (DAB), Fvs, or single chain Fvs (scFv).

Methods of making and using polyclonal and monoclonal antibodies are well known in the art, e.g., in Harlow et al., *Using Antibodies: A Laboratory Manual: Portable Protocol I*. Cold Spring Harbor Laboratory (Dec. 1, 1998). Methods for making modified antibodies and antibody fragments (e.g., chimeric antibodies, reshaped antibodies, humanized antibodies, or fragments thereof, e.g., Fab', Fab, F(ab')$_2$ fragments); or biosynthetic antibodies (e.g., single chain antibodies, single domain antibodies (DABs), Fv, single chain Fv (scFv), and the like), are known in the art and can be found, e.g., in Zola, *Monoclonal Antibodies: Preparation and Use of Monoclonal Antibodies and Engineered Antibody Derivatives*, Springer Verlag (Dec. 15, 2000; 1st edition).

In some instances, the antibodies recognize tumor specific epitopes (e.g., TAG-72 (Kjeldsen et al., *Cancer Res.*, 48:2214-2220 (1988); U.S. Pat. Nos. 5,892,020; 5,892,019; and 5,512,443); human carcinoma antigen (U.S. Pat. Nos. 5,693,763; 5,545,530; and 5,808,005); TP1 and TP3 antigens from osteocarcinoma cells (U.S. Pat. No. 5,855,866); Thomsen-Friedenreich (TF) antigen from adenocarcinoma cells (U.S. Pat. No. 5,110,911); "KC-4 antigen" from human prostrate adenocarcinoma (U.S. Pat. Nos. 4,708,930 and 4,743, 543); a human colorectal cancer antigen (U.S. Pat. No. 4,921, 789); CA125 antigen from cystadenocarcinoma (U.S. Pat. No. 4,921,790); DF3 antigen from human breast carcinoma (U.S. Pat. Nos. 4,963,484 and 5,053,489); a human breast tumor antigen (U.S. Pat. No. 4,939,240); p97 antigen of human melanoma (U.S. Pat. No. 4,918,164); carcinoma or orosomucoid-related antigen (CORA) (U.S. Pat. No. 4,914, 021); a human pulmonary carcinoma antigen that reacts with human squamous cell lung carcinoma but not with human small cell lung carcinoma (U.S. Pat. No. 4,892,935); T and Tn haptens in glycoproteins of human breast carcinoma (Springer et al., *Carbohydr. Res.*, 178:271-292 (1988)), MSA breast carcinoma glycoprotein (Tjandra et al., *Br. J. Surg.*, 75:811-817 (1988)); MFGM breast carcinoma antigen (Ishida et al., *Tumor Biol.*, 10: 12-22 (1989)); DU-PAN-2 pancreatic carcinoma antigen (Lan et al., *Cancer Res.*, 45:305-310 (1985)); CA125 ovarian carcinoma antigen (Hanisch et al., *Carbohydr. Res.*, 178:29-47 (1988)); and YH206 lung carcinoma antigen (Hinoda et al., *Cancer J.*, 42:653-658 (1988)).

For example, to target breast cancer cells, the nanoparticles can include, as a targeting agent, folic acid, EGF, FGF, and antibodies (or antibody fragments) to the tumor-associated antigens MUC 1, cMet receptor and CD56 (NCAM).

Other antibodies that can be used recognize specific pathogens (e.g., *Legionella peomophilia, Mycobacterium tuberculosis, Clostridium tetani, Hemophilus influenzae, Neisseria gonorrhoeae, Treponema pallidum, Bacillus anthracis, Vibrio cholerae, Borrelia burgdorferi, Cornebacterium diphtheria, Staphylococcus aureus*, human papilloma virus, human immunodeficiency virus, rubella virus, and polio virus).

Antibodies or ligands that can be attached to the nanoparticles described herein include, without limitation, antibodies to IL2 receptor a, complement system protein C5, CD11a, CD20, TNF-alpha, T cell CD3 receptor, T cell VLA4 receptor, F protein of RSV, epidermal growth factor receptor, vascular endothelial growth factor, glycoprotein IIb/IIIa, CD52, and epidermal growth factor receptor.

Antibody attachment to nanoparticles can be performed through standard covalent binding to free amine groups (see, e.g., Torchilin et al. (1987) *Hybridoma*, 6:229-240; Torchilin, et al., (2001) *Biochim. Biophys. Acta*, 1511:397-411; Masuko, et al., (2005), *Biomacromol.*, 6:800-884) in the outermost layer of a polymer described herein. Standard methods of protein covalent binding are known, such as covalent binding through amine groups. This methodology can be found in, e.g., *Protein Architecture: Interfacing Molecular Assemblies and Immobilization*, editors: Lvov et al. (2000) Chapter 2, pp. 25-54.

To activate the polymer coat of the particle, a polymer can be used that has free amino, carboxy, SH-, epoxy-, and/or other groups that can react with ligand molecules directly or after preliminary activation with, e.g., carbodiimides, SPDP, SMCC, and/or other mono- and bifunctional reagents. Alternatively, a polymer can be functionalized to contain one of these groups by methods known in the art.

Signal Peptides as Targeting Agents

In some instances, the targeting agents include a signal peptide. These peptides can be chemically synthesized or cloned, expressed and purified using known techniques. Signal peptides can be used to target the nanoparticles described herein to a discreet region within a cell. In some situations, specific amino acid sequences are responsible for targeting the nanoparticles into cellular organelles and compartments. For example, the signal peptides can direct a nanoparticle described herein into mitochondria. In other examples, a nuclear localization signal is used.

Nucleic Acids as Targeting Agents

In other instances, the targeting agent is a nucleic acid (e.g., RNA or DNA). In some examples, the nucleic acid targeting agents are designed to hybridize by base pairing to a particular nucleic acid (e.g., chromosomal DNA, mRNA, or ribosomal RNA). In other situations, the nucleic acids bind a ligand or biological target. For example, the nucleic acid can bind reverse transcriptase, Rev or Tat proteins of HIV (Tuerk et al., *Gene,* 137(1):33-9 (1993)); human nerve growth factor (Binkley et al., *Nuc. Acids Res.,* 23(16):3198-205 (1995)); or vascular endothelial growth factor (Jellinek et al., *Biochem.,* 83(34): 10450-6 (1994)). Nucleic acids that bind ligands can be identified by known methods, such as the SELEX procedure (see, e.g., U.S. Pat. Nos. 5,475,096; 5,270,163; and 5,475,096; and WO 97/38134; WO 98/33941; and WO 99/07724). The targeting agents can also be aptamers that bind to particular sequences.

Antisense and Ribozymes

Other agents that are useful in the methods described herein are nucleic acids, including antisense molecules or catalytic nucleic acid molecules (e.g., ribozymes) that specifically hybridize mRNA encoding a target polypeptide. An antisense construct includes the reverse complement of at least part of the cDNA coding sequence or mRNA of a target polypeptide, the target polypeptide cDNA, or gene sequence or flanking regions thereof, and thus it can hybridize to the mRNA.

The introduced sequence need not be the full-length cDNA or gene or reverse complement thereof, and need not be exactly homologous to the equivalent sequence found in the cell type to be transformed. Antisense molecules can be made using known techniques in the art (see, e.g., Agrawal, *Methods in Molecular Biology*, Humana Press Inc., 1993, Vol. 20 ("Protocols for Oligonucleotides and Analogs")).

The antisense molecule may be conjugated to another molecule, e.g., a peptide, hybridization triggered cross-linking agent, transport agent, aptamer, or hybridization-triggered cleavage agent. A targeting moiety can also be included that enhances uptake of the molecule by cells. The targeting moiety can be a specific binding molecule, such as an antibody or fragment thereof that recognizes a molecule present on the surface of the cell.

Alternatively, the agent is a catalytic nucleic acid, such as a ribozyme (a synthetic RNA molecule that possesses highly specific endoribonuclease activity). The production and use of ribozymes are disclosed in, e.g., U.S. Pat. No. 4,987,071 and U.S. Pat. No. 5,543,508. Ribozymes can be synthesized and administered to a cell or a subject, or can be encoded on an expression vector, from which the ribozyme is synthesized in the targeted cell (see, e.g., WO 9523225, and Beigelman et al., *Nucl. Acids Res.* 23:4434-42, 1995). Examples of oligonucleotides with catalytic activity are described in, e.g., WO 9506764 and WO 9011364, and Sarver et al., *Science* 247: 1222-1225, 1990. The inclusion of ribozyme sequences within antisense RNAs can be used to confer RNA cleaving activity on the antisense RNA, such that endogenous mRNA molecules that bind to the antisense RNA are cleaved, which, in turn, leads to an enhanced antisense inhibition of endogenous gene expression.

RNA Interference

Double-stranded nucleic acid molecules that can silence a gene encoding a target polypeptide can also be used as agents in the methods described herein. RNA interference (RNAi) is a mechanism of post-transcriptional gene silencing in which double-stranded RNA (dsRNA) corresponding to a gene (or coding region) of interest is introduced into a cell or an organism, resulting in degradation of the corresponding mRNA. The RNAi effect persists for multiple cell divisions before gene expression is regained. RNAi is therefore an effective method for making targeted knockouts or "knockdowns" at the RNA level. RNAi has proven successful in human cells, including human embryonic kidney and HeLa cells (see, e.g., Elbashir et al., *Nature* 411:494-498, 2001). For example, gene silencing can be induced in mammalian cells by the endogenous expression of RNA hairpins (see Paddison et al., *PNAS (USA)* 99:1443-1448, 2002). In another instances, transfection of small (21-23 nt) dsRNA specifically inhibits gene expression (reviewed in Caplen, *Trends Biotechnol.* 20:49-51, 2002).

Briefly, RNAi is thought to work as follows. miRNA, pre-miRNA, pri-miRNA, or dsRNA corresponding to a portion of a gene to be silenced is introduced into a cell. The dsRNA is digested into 21-23 nucleotide siRNAs, or short interfering RNAs. The siRNA duplexes bind to a nuclease complex to form what is known as the RNA-induced silencing complex, or RISC. The RISC targets the homologous transcript by base pairing interactions between one of the siRNA strands and the endogenous mRNA. It then cleaves the mRNA approximately 12 nucleotides from the 3' terminus of the siRNA (reviewed in Sharp et al., *Genes Dev.* 15: 485-490, 2001; and Hammond et al., *Nature Rev. Gen.* 2: 110-119, 2001).

RNAi technology in gene silencing utilizes standard molecular biology methods. dsRNA corresponding to the sequence from a target gene to be inactivated can be produced by standard methods, e.g., by simultaneous transcription of both strands of a template DNA (corresponding to the target sequence) with T7 RNA polymerase. Kits for production of dsRNA for use in RNAi are available commercially, e.g., from New England Biolabs, Inc. Methods of transfection of dsRNA or plasmids engineered to make dsRNA are routine in the art.

Gene silencing effects similar to those of RNAi have been reported in mammalian cells with transfection of a mRNA-cDNA hybrid construct (Lin et al., *Biochem. Biophys. Res. Commun.* 281:639-644, 2001), and can be used as another method for gene silencing. Therapeutic applications of RNAi are described, e.g., in Shuey, *Drug Discov. Today* 7:1040-1046, 2002.

Aptamers

In some instances, the agent is an aptamer that targets a particular polypeptide. Aptamers are nucleic acid molecules having a tertiary structure that permits them to specifically bind to protein ligands (see, e.g., Osborne et al., *Curr. Opin. Chem. Biol.* 1:5-9, 1997; and Patel, *Curr. Opin. Chem. Biol.* 1:32-46, 1997). Aptamers can also be conjugated to siRNA or miRNA (see WO 2007/143086).

Aptamers may be created using a type of in vitro natural selection for randomly-generated nucleic acid sequences that bind to the selected target. This method has been termed "SELEX" (for Systematic Evolution of Ligands by Exponential Enrichment). The SELEX method (hereinafter termed SELEX) and related application are described in, e.g., U.S. Pat. No. 5,475,096, U.S. Pat. No. 6,083,696, U.S. Pat. No. 6,441,158 and U.S. Pat. No. 6,458,559. The SELEX process provides a class of products that are referred to as nucleic acid ligands, such ligands having a unique sequence, and that have the property of binding specifically to a desired target compound or molecule. Each SELEX-identified nucleic acid ligand is a specific ligand of a given target compound or molecule. SELEX is based on the insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric.

Briefly, the SELEX method involves selection from a mixture of candidates and step-wise iterations of binding, partitioning, and amplification, using the same general selection theme, to achieve virtually any desired criterion of binding affinity and selectivity. Starting from a mixture of nucleic acids, preferably comprising a segment of randomized sequence, the method includes contacting the mixture with the target under conditions favorable for binding, partitioning unbound nucleic acids from those nucleic acids which have bound to target molecules, dissociating the nucleic acid-target pairs, amplifying the nucleic acids dissociated from the nucleic acid-target pairs to yield a ligand-enriched mixture of nucleic acids, then reiterating the steps of binding, partitioning, dissociating and amplifying through as many cycles as desired. A variety of techniques can be used to partition members in the pool of nucleic acids that have a higher affinity to the target than the bulk of the nucleic acids in the mixture.

While not bound by theory, SELEX is based on the observation that within a nucleic acid mixture containing a large number of possible sequences and structures there is a wide range of binding affinities for a given target. A nucleic acid mixture comprising, for example, a 20-nucleotide randomized segment, can have 420 candidate possibilities. Those that have the higher affinity constants for the target are most likely to bind to the target. After the partitioning, dissociating and amplifying steps, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested for binding affinity as pure ligands.

Cycles of selection, partition and amplification are repeated until a desired goal is achieved. In the most general case, selection, partition and amplification is continued until no significant improvement in binding strength is achieved on repetition of the cycle. The method may be used to sample as many as about $10^{18}$ different nucleic acid species. The nucleic acids of the test mixture preferably include a randomized sequence portion as well as conserved sequences necessary for efficient amplification. Nucleic acid sequence variants can be produced in a number of ways including synthesis of randomized nucleic acid sequences and size selection from randomly cleaved cellular nucleic acids. The variable sequence portion may contain fully or partially random sequence; it may also contain subportions of conserved sequence incorporated with randomized sequence. Sequence variation in test nucleic acids can be introduced or increased by mutagenesis before or during the selection, partition and amplification iterations.

The basic SELEX method may be modified to achieve specific objectives. For example, U.S. Pat. No. 5,707,796 describes the use of SELEX in conjunction with gel electrophoresis to select nucleic acid molecules with specific structural characteristics, such as bent DNA. U.S. Pat. No. 5,763,177 describes a SELEX based method for selecting nucleic acid ligands containing photoreactive groups capable of binding and/or photocrosslinking to and/or photoinactivating a target molecule. U.S. Pat. No. 5,580,737 describes a method for identifying highly specific nucleic acid ligands able to discriminate between closely related molecules, termed "counter-SELEX". U.S. Pat. No. 5,567,588 describes a SELEX-based method which achieves highly efficient partitioning between oligonucleotides having high and low affinity for a target molecule.

The SELEX method encompasses the identification of high-affinity nucleic acid ligands containing modified nucleotides conferring improved characteristics on the ligand, such as improved in vivo stability or delivery. Examples of such modifications include chemical substitutions at the ribose and/or phosphate and/or base positions. Specific SELEX-identified nucleic acid ligands containing modified nucleotides are described in, e.g., U.S. Pat. No. 5,660,985, which describes oligonucleotides containing nucleotide derivatives chemically modified at the 5- and 2'-positions of pyrimidines, as well as specific RNA ligands to thrombin containing 2'-amino modifications. Also included are highly specific nucleic acid ligands containing one or more nucleotides modified with 2'-amino ($2'-NH_2$), 2'-fluoro (2'-F), and/or 2'-O-methyl (2'-OMe).

Other Targeting Agents

The targeting agents can recognize a variety of epitopes on preselected biological targets (e.g., pathogens, tumor cells, or normal cells). For example, in some instances, the targeting agent can be sialic acid to target HIV (Wies et al., *Nature*, 333:426 (1988)), influenza (White et al., *Cell*, 56:725 (1989)), *Chlamydia* (*Infect. Immunol*, 57:2378 (1989)), *Neisseria meningitidis, Streptococcus suis, Salmonella*, mumps, newcastle, reovirus, Sendai virus, and myxovirus; and 9-OAC sialic acid to target coronavirus, encephalomyelitis virus, and rotavirus; non-sialic acid glycoproteins to target cytomegalovirus (*Virology*, 176:337 (1990)) and measles virus (*Virology*, 172:386 (1989)); CD4 (Khatzman et al., *Nature*, 312:763 (1985)), vasoactive intestinal peptide (Sacerdote et al., *J. Neurosci. Res.* 18:102 (1987)), and peptide T (Ruff et al., *FEBS Letters*, 211:17 (1987)) to target HIV; epidermal growth factor to target vaccinia (Epstein et al., *Nature*, 318: 663 (1985)); acetylcholine receptor to target rabies (Lentz et al., *Science* 215: 182 (1982)); Cd3 complement receptor to target Epstein-Barr virus (Carel et al., *J. Biol. Chem.*, 265: 12293 (1990)); .beta.-adrenergic receptor to target reovirus (Co et al., *Proc. Natl. Acad. Sci. USA*, 82:1494 (1985)); ICAM-1 (Marlin et al., *Nature*, 344:70 (1990)), N-CAM, and myelin-associated glycoprotein MAb (Shephey et al., *Proc. Natl. Acad. Sci. USA*, 85:7743 (1988)) to target rhinovirus; polio virus receptor to target polio virus (Mendelsohn et al., *Cell*, 56:855 (1989)); fibroblast growth factor receptor to target herpes virus (Kaner et al., *Science*, 248:1410 (1990)); oligomannose to target *E. coli*; and ganglioside $G_{M1}$ to target *Neisseria meningitides*.

In other instances, the targeting agent targets nanoparticles to factors expressed by oncogenes. These can include, but are not limited to, tyrosine kinases (membrane-associated and cytoplasmic forms), such as members of the Src family; serine/threonine kinases, such as Mos; growth factor and receptors, such as platelet derived growth factor (PDDG), SMALL GTPases (G proteins), including the ras family, cyclin-dependent protein kinases (cdk), members of the myc family members, including c-myc, N-myc, and L-myc, and bcl-2 family members.

In addition, vitamins (both fat soluble and non-fat soluble vitamins) can be used as targeting agents to target biological targets (e.g., cells) that have receptors for, or otherwise take up, vitamins. For example, fat soluble vitamins (such as vitamin D and its analogs, vitamin E, vitamin A), and water soluble vitamins (such as vitamin C and vitamin B9 (folic acid)) can be used as targeting agents.

Therapeutic Agents

In some instances, a nanoparticle described herein can include a compound that is a therapeutic agent. Useful therapeutic agents are known to treat selected disorders. They can be, but are not limited to, steroids, analgesics, local anesthetics, antibiotic agents, chemotherapeutic agents, immunosuppressive agents, anti-inflammatory agents, antiproliferative agents, antimitotic agents, angiogenic agents, antipsychotic agents, central nervous system (CNS) agents; anticoagulants, fibrinolytic agents, growth factors, antibodies, ocular drugs, and metabolites, analogs, derivatives, fragments, and purified, isolated, recombinant and chemically synthesized versions of these species, and combinations thereof.

Representative useful therapeutic agents include, but are not limited to, tamoxifen, paclitaxel, doxorubicin, low soluble anticancer drugs, camptothecin and its derivatives, e.g., topotecan and irinotecan, KRN 5500 (KRN), mesotetraphenylporphine, dexamethasone, benzodiazepines, allopurinol, acetohexamide, benzthiazide, chlorpromazine, chlordiazepoxide, haloperidol, indomethacine, lorazepam, methoxsalen, methylprednisone, nifedipine, oxazepam, oxyphenbutazone, prednisone, prednisolone, pyrimethamine, phenindione, sulfisoxazole, sulfadiazine, temazepam, sulfamerazine, ellipticin, porphine derivatives for photo-dynamic therapy, and/or trioxsalen, as well as all mainstream antibiotics, including the penicillin group, fluoroquinolones, and first, second, third, and fourth generation cephalosporins. These agents are commercially available from, e.g., Merck & Co., Barr Laboratories, Avalon Pharma, and Sun Pharma, among others.

Other therapeutic agents include antisense agents, ribozymes, RNAi agents, such as siRNA, and aptamers, as described herein.

Imaging Agents

In some instances, a nanoparticle described herein includes an imaging agent. As used herein, the term "imaging agent" refers to a compound that can be detected. Examples of imaging agents include magnetic resonance imaging contrast agents, computed tomography (CT scan) imaging agents, optical imaging agents and radioisotopes. In certain instances, an imaging agent is present in a nanoparticle described herein with a therapeutic agent. In other instances, an imaging agent is included in a nanoparticle in the absence of a therapeutic agent.

The imaging agent is linked to a polymer described herein. For example, a polymer described herein can be conjugated to diethylene triamine pentaacetic acid (DTPA) using methods known in the art, and the imaging agent can be linked to the DTPA.

In particular instances, a nanoparticle library described herein includes polymers having varying degrees of DTPA saturation. For example, about 10% of the polymers can be conjugated with DTPA, about 20%, about 30%, about 40%, about 50%, about 60%, about 70%, about 80%, about 90%, or about 100% of the polymers can be conjugated with DTPA.

Nonlimiting examples of imaging agents that can be used in the methods and compositions described herein include radionuclides (e.g., $^{64}$Gd, $^{111}$In, $^{99m}$Tc, $^{90}$Y, $^{125}$I, and $^{166}$Ho), iron oxide, and quantum dots. Other imaging agents include fluorophores, such as fluorescein or dansyl.

Methods of Making Nanoparticle Libraries

Due to the diversity of potential therapeutic agents, each having different physicochemical properties, a modular platform is used to synthesize and to identify an appropriate nanoparticle delivery system customized to the properties of a particular therapeutic agent and a particular biological target. Combinatorial formulation libraries of functional components allow for development of a library containing a relatively small number of potential nanoparticles compared to traditional libraries, which can be subsequently screened using, e.g., a high-throughput system.

At least three of the functional components described herein can be used to make the nano-formulations. The libraries are designed based on selecting appropriate components and weight ratios of each in the final nano-assembly. The physicochemical properties of the therapeutic agent are used to select the appropriate components. For example, a hydrophobic core (e.g., comprising a hydrophobic agent described herein) can be used to encapsulate hydrophobic therapeutic agents, while a hydrophilic core (e.g., comprising a hydrophilic agent described herein) can be used to encapsulate hydrophilic therapeutic agents.

In particular instances, a water-soluble polymer is derivatized with a suitable fatty acid. A $C_2$-$C_{14}$ fatty acid can be selected to derivatize a polymer when a therapeutic agent is hydrophilic, and a $C_{14}$-$C_{28}$ fatty acid can be selected to derivatize a polymer when a therapeutic agent is hydrophobic. Methods of determining the hydrophobicity or hydrophilicity of a therapeutic agent are known in the art. One nonlimiting example to determine the hydrophobicity or hydrophilicity of a therapeutic agent is by measuring the partition coefficient of the therapeutic agent. As used herein, "partition coefficient" refers to a measure of how well a substance partitions between a lipid (oil) and water. The partition coefficient can be measured by determining the ratio of the equilibrium concentrations of a dissolved substance in a two-phase system consisting of two largely immiscible solvents, such as water and n-octanol (see, e.g., Sangster, *Octanol-Water Partition Coefficients: Fundamentals and Physical Chemistry*, John Wiley & Sons (1997)). In the methods described herein, a therapeutic agent is hydrophilic if the partition coefficient is less than about 100, and is hydrophobic if the partition coefficient is greater than about 100.

Generally, a customized nanoparticle library can be made by first solubilizing a therapeutic agent in an aqueous solution. Selecting an appropriate aqueous solution is within the skill of those in the art, and any aqueous solution that solubilizes a therapeutic agent can be used.

Next, a polymer is derivatized with an appropriate fatty acid. In some instances, if the therapeutic agent is hydrophilic, a $C_2$-$C_{14}$ fatty acid can be selected to derivatize the polymer, and when a therapeutic agent is hydrophilic, and a $C_{14}$-$C_{28}$ fatty acid can be selected to derivatize the polymer. In particular situations, the polymer is also conjugated with PEG, as described herein.

The solubilized therapeutic agent and the derivatized polymer are then combined, resulting in the self-assembly of nanoparticles, in which the polymer forms a hydrogel shell surrounding the therapeutic agent. By varying the concentrations or the types of the polymer, the fatty acid, and/or the PEG, different nanoparticles are formed, resulting in a customized library of different types of nanoparticles.

In certain situations, such as when the nanoparticle is formulated for in vivo delivery, the polymer can be crosslinked using a crosslinking agent described herein. In some situations, two populations of polymer can be combined: a first population of crosslinked polymer and a second population of fatty acid-derivatized polymer. These polymers are then combined with the solubilized therapeutic agent and PEG as described herein, to result in a self-assembled nanoparticle.

When a targeting agent is included in a nanoparticle, the PEG can be activated and derivatized with the appropriate targeting agent, as described herein. Combining a fatty acid-derivatized polymer, target agent-conjugated PEG, and solubilized therapeutic agent results in the self-assembly of these components into nanoparticles, having a hydrogel shell of polymer surrounding a core (containing the therapeutic agent), with PEG linked by one end to the hydrogel shell and linked by the other end to the targeting agent.

In one exemplary method, thiol-modified dextrans are synthesized to promote intermolecular disulfide crosslinking and that can stabilize the formed nanostructures in plasma upon systemic administration. Due to higher intracellular glutathione level, the disulfide crosslinks can be broken in the cells to promote release of the therapeutic agent from the nanoparticle into the cytoplasm of a cell. In another exemplary method, PEG-modified dextrans can be used to allow for long circulation and passive targeted delivery to tumor mass due to enhanced permeability and retention effect.

Figure 2:
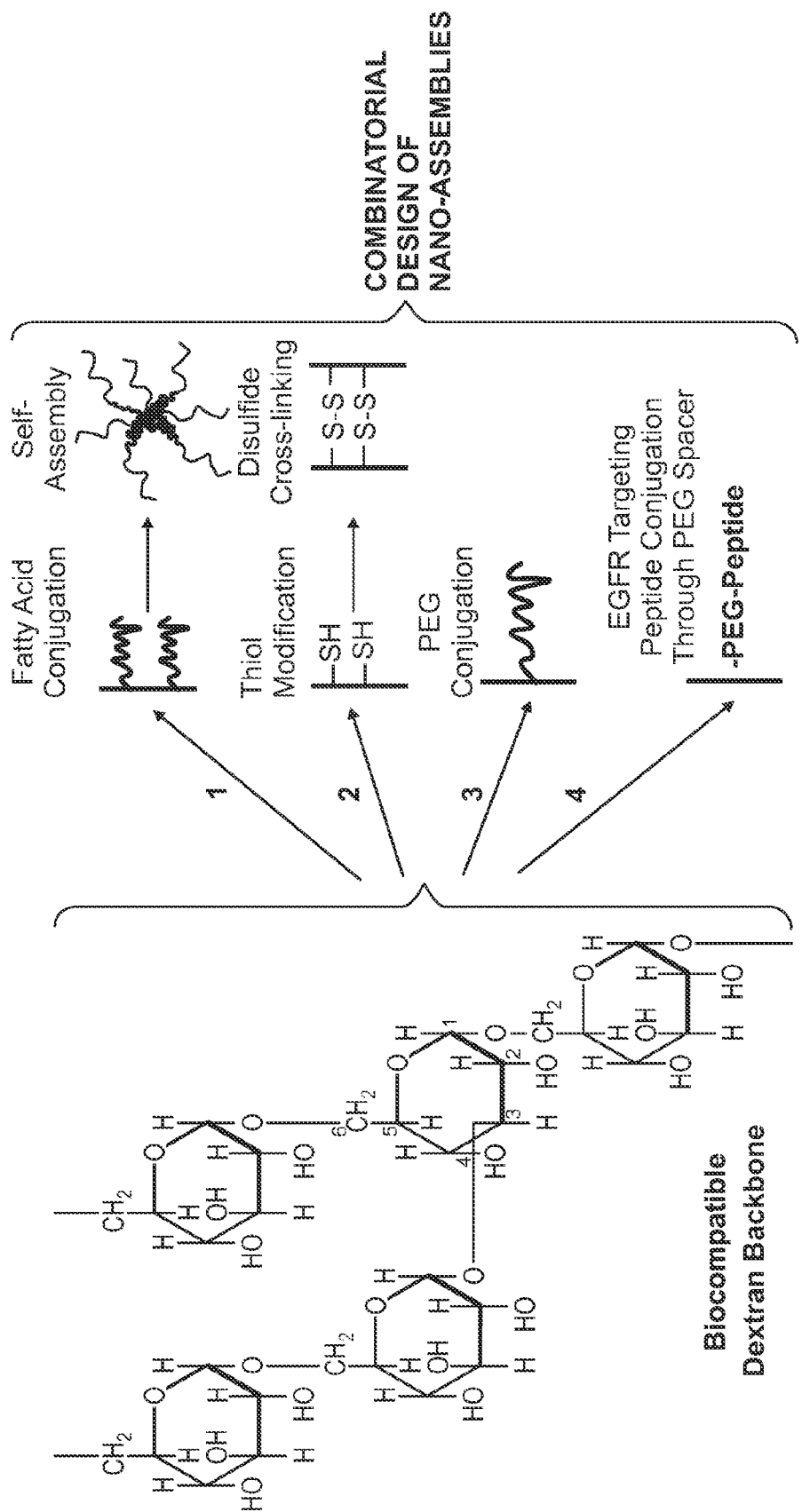
FIG. 2 is a schematic illustration of combinatorial designed nano-platform systems.

In another exemplary method, illustrated in FIG. 2, different types of polymer-based nanoparticles are synthesized and included in the library. Each of the functional blocks can be mixed in aqueous media for fabrication of self-assembled nanostructures. The type of functional block, degree of derivatization of the polymer, the concentration of each derivative, and the weight ratio of each can be varied to develop a combinatorial library, e.g., having up to about 5,000 to about 7,000 different nanoparticles. Based on the size, surface charge, and stability of the nanoparticles, formulations can be selected for encapsulation of therapeutic agents. The physicochemical properties of functional macrostructures can be matched with the physicochemical properties of an encapsulated therapeutic agent to identify optimal formulations for a particular therapeutic agent.

Methods of Screening Nanoparticle Libraries

Figure 3:
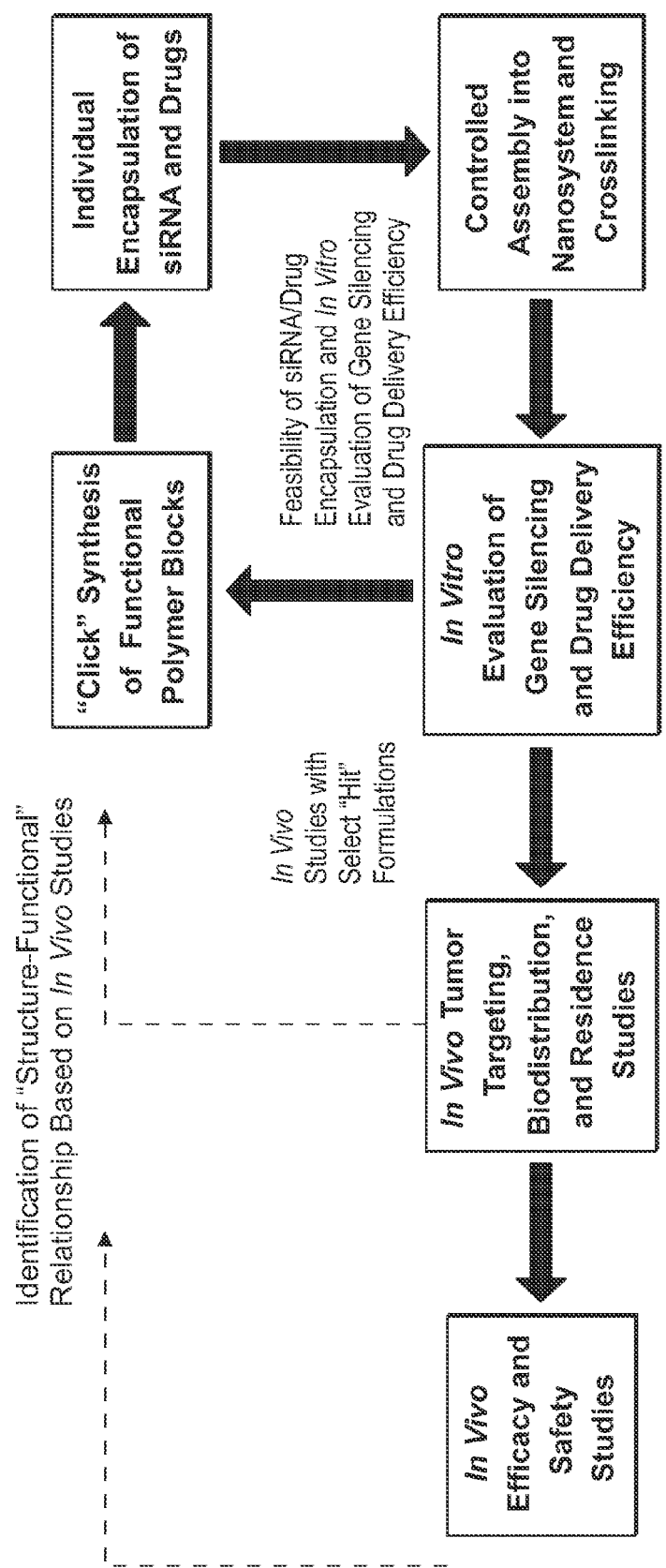
FIG. 3 is a schematic illustration of a combinatorial approach to development of self-assembled nano-platforms for combination siRNA and drug delivery.

The nanoparticle libraries described herein can be screened to identify candidate nanoparticles customized for a particular therapeutic agent and/or for a particular delivery. One exemplary screening method is depicted in FIG. 3.

Initially, the stability of the nanoparticles can be assessed using methods known in the art. For example, fluorescently-labeled therapeutic agents, hydrophilic fluorophores, or hydrophobic fluorophores can be used for initial screening of encapsulation and stability of the nanoparticles. Based on this initial screen, nanoparticles that demonstrate appropriate encapsulation can be further modified with PEG and/or a targeting agent, and the nanoparticles can be screened in known in vitro assays, such as using cell lines. Additional polymer derivatives can be designed and synthesized based on the in vitro studies, and a cycle of combinatorial formulation development and preliminary evaluation can be performed to identify select "hit" formulations for in vivo testing.

Following optimization of nanoparticles in vitro, in vivo studies can be undertaken. In one exemplary method, the nanoparticles are evaluated for tumor targeting efficiency, residence, and biodistribution profiles in vivo in animal models. Additionally, formulations identified as exhibiting enhanced tumor accumulation can be tested in an efficacy screen using administration of the nanoparticle alone and in combination with a therapeutic agent administered systemically. The in vivo acute safety profile can be examined, e.g., by measuring body weight changes, blood cell counts, liver enzyme levels, and liver tissue histopathology.

An exemplary 1000 polymer library was generated for screening and selecting appropriate hits. Table 1 shows non-limiting examples of polymers and targeting agents for the synthesis of such a library.

TABLE 1

| Neutral or Anionic Polymer (backbone) | Crosslinking Agent | Hydrophobic Group (lipid) | PEG | Targeting Agents |
|---|---|---|---|---|
| Dextran | Cystamine | Derivatives of stearic acid (e.g., sterylamine) | PEG 2000 | Peptides |
| Inulin | 2-imunothiolane | Oleic acid/oleylamine | PEG 5000 | FAB/antibody |
| Ficoll | Cystamine hydrochloride | Laurylamine | PEG monomethyl ether Mw 550 | Aptamers |
| Water-Soluble Starch | | Butylamine | PEG monomethyl ether Mw 750 | Folic acid |
| Alginate | | Hexylamine | PEG 2000 heterobifunctional NHS and Malemide activate | |
| Poly(vinyl alcohol) | | Dodecylamine | PEG 2000 NHS | |
| Dextran | | Poly(proplylene glycol-methyl ether acrylate | PEG acrylates of varying mol. wt | |
| Dextran | | Neopentyl glycol metyl ether propoxylate | PEG phenyl ether acrylate Mw 236 | |
| Dextran | | Palmitic acid/chloride | PEG methyl ether acrylate mw454 | |
| Dextran | | PCL-diol | PEG methyl ether acrylate mw 1100 | |
| Dextran | | PLGA-diol | PEG-SH | |

Diseases and Disorders

The nanoparticles described herein can be used to treat (e.g., mediate the translocation of drugs into) diseased cells and tissues. In this regard, various diseases are amenable to treatment using the nanoparticles and methods described herein. An exemplary, nonlimiting list of diseases that can be treated with the subject nanoparticles includes breast cancer; prostate cancer; lung cancer; lymphomas; skin cancer; pancreatic cancer; colon cancer; melanoma; ovarian cancer; brain cancer; head and neck cancer; liver cancer; bladder cancer; non-small lung cancer; cervical carcinoma; leukemia; non-Hodgkins lymphoma, multiple sclerosis, neuroblastoma and glioblastoma; T and B cell mediated autoimmune diseases; inflammatory diseases; infections; infectious diseases; hyperproliferative diseases; AIDS; degenerative conditions; cardiovascular diseases (including coronary restenosis); diabetes; transplant rejection; and the like. In some cases, the treated cancer cells are metastatic.

In particular instances, a nanoparticle described herein can be used to reverse multi-drug resistance (MDR). For examples, downregulation of MDR transporter and anti-apoptotic genes such as Bcl-2, survivin, mdr-1, or mrp-1 by siRNA-containing nanoparticles can be used.

Therapeutic Administration

The route and/or mode of administration of a nanoparticle described herein can vary depending upon the desired results. Dosage regimens can be adjusted to provide the desired response, e.g., a therapeutic response.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. The mode of administration is left to the discretion of the practitioner.

In some instances, a nanoparticle described herein is administered locally. This is achieved, for example, by local infusion during surgery, topical application (e.g., in a cream or lotion), by injection, by means of a catheter, by means of a suppository or enema, or by means of an implant, said implant being of a porous, non-porous, or gelatinous material, including membranes, such as sialastic membranes, or fibers. In some situations, a nanoparticle described herein is introduced into the central nervous system, circulatory system or gastrointestinal tract by any suitable route, including intraventricular, intrathecal injection, paraspinal injection, epidural injection, enema, and by injection adjacent to the peripheral nerve. Intraventricular injection can be facilitated by an intraventricular catheter, for example, attached to a reservoir, such as an Ommaya reservoir.

This disclosure also features a device for administering a nanoparticle described herein. The device can include, e.g., one or more housings for storing pharmaceutical compositions, and can be configured to deliver unit doses of a nanoparticle described herein.

Pulmonary administration can also be employed, e.g., by use of an inhaler or nebulizer, and formulation with an aerosolizing agent, or via perfusion in a fluorocarbon or synthetic pulmonary surfactant.

In some instances, a nanoparticle described herein can be delivered in a vesicle, in particular, a liposome (see Langer, *Science* 249:1527-1533 (1990) and Treat et al., *Liposomes in the Therapy of Infectious Disease and Cancer*, pp. 317-327 and pp. 353-365 (1989)).

In yet other situations, a nanoparticle described herein can be delivered in a controlled-release system or sustained-release system (see, e.g., Goodson, in *Medical Applications of Controlled Release*, 2:115-138 (1984)). Other controlled or sustained-release systems discussed in the review by Langer, *Science* 249:1527-1533 (1990) can be used. In one case, a pump can be used (Langer, *Science* 249:1527-1533 (1990); Sefton, *CRC Crit. Ref Biomed. Eng.* 14:201 (1987); Buchwald et al., *Surgery* 88:507 (1980); and Saudek et al., *N. Engl. J. Med.* 321:574 (1989)).

In yet other situations, a controlled- or sustained-release system can be placed in proximity of a target of nanoparticle described herein, reducing the dose to a fraction of the systemic dose.

A nanoparticle described herein can be formulated as a pharmaceutical composition that includes a suitable amount of a physiologically acceptable excipient (see, e.g., *Remington's Pharmaceutical Sciences* pp. 1447-1676 (Alfonso R. Gennaro, ed., 19th ed. 1995)). Such physiologically acceptable excipients can be, e.g., liquids, such as water and oils, including those of petroleum, animal, vegetable, or synthetic origin, such as peanut oil, soybean oil, mineral oil, sesame oil and the like. The physiologically acceptable excipients can be saline, gum acacia, gelatin, starch paste, talc, keratin, colloidal silica, urea and the like. In addition, auxiliary, stabilizing, thickening, lubricating, and coloring agents can be used. In one situation, the physiologically acceptable excipients are sterile when administered to an animal. The physiologically acceptable excipient should be stable under the conditions of manufacture and storage and should be preserved against the contaminating action of microorganisms. Water is a particularly useful excipient when a nanoparticle described herein is administered intravenously. Saline solutions and aqueous dextrose and glycerol solutions can also be employed as liquid excipients, particularly for injectable solutions. Suitable physiologically acceptable excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Other examples of suitable physiologically acceptable excipients are described in *Remington's Pharmaceutical Sciences pp.* 1447-1676 (Alfonso R. Gennaro, ed., 19th ed. 1995). The pharmaceutical compositions, if desired, can also contain minor amounts of wetting or emulsifying agents, or pH buffering agents.

Liquid carriers can be used in preparing solutions, suspensions, emulsions, syrups, and elixirs. A nanoparticle described herein can be suspended in a pharmaceutically acceptable liquid carrier such as water, an organic solvent, a mixture of both, or pharmaceutically acceptable oils or fat. The liquid carrier can contain other suitable pharmaceutical additives including solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particular containing additives described herein, e.g., cellulose derivatives, including sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. The liquid carriers can be in sterile liquid form for administration. The liquid carrier for pressurized compositions can be halogenated hydrocarbon or other pharmaceutically acceptable propellant.

In other instances, a nanoparticle described herein is formulated for intravenous administration. Compositions for intravenous administration can comprise a sterile isotonic aqueous buffer. The compositions can also include a solubilizing agent. Compositions for intravenous administration can optionally include a local anesthetic such as lignocaine to lessen pain at the site of the injection. The ingredients can be supplied either separately or mixed together in unit dosage form, for example, as a dry lyophilized powder or water-free concentrate in a hermetically sealed container such as an ampule or sachette indicating the quantity of active agent. Where a nanoparticle described herein is administered by infusion, it can be dispensed, for example, with an infusion bottle containing sterile pharmaceutical grade water or saline. Where a nanoparticle described herein is administered by injection, an ampule of sterile water for injection or saline can be provided so that the ingredients can be mixed prior to administration.

In other circumstances, a nanoparticle described herein can be administered across the surface of the body and the inner linings of the bodily passages, including epithelial and mucosal tissues. Such administrations can be carried out using a nanoparticle described herein in lotions, creams, foams, patches, suspensions, solutions, and suppositories (e.g., rectal or vaginal). In some instances, a transdermal patch can be used that contains a nanoparticle described herein and a carrier that is inert to the nanoparticle described herein, is non-toxic to the skin, and that allows delivery of the agent for systemic absorption into the blood stream via the skin. The carrier can take any number of forms such as creams or ointments, pastes, gels, or occlusive devices. The creams or ointments can be viscous liquid or semisolid emulsions of either the oil-in-water or water-in-oil type. Pastes of absorptive powders dispersed in petroleum or hydrophilic petroleum containing a nanoparticle described herein can also be used. A variety of occlusive devices can be used to release a nanoparticle described herein into the blood stream, such as a semi-permeable membrane covering a reservoir containing the nanoparticle described herein with or without a carrier, or a matrix containing the nanoparticle described herein.

A nanoparticle described herein can be administered rectally or vaginally in the form of a conventional suppository. Suppository formulations can be made using methods known to those in the art from traditional materials, including cocoa butter, with or without the addition of waxes to alter the suppository's melting point, and glycerin. Water-soluble suppository bases, such as polyethylene glycols of various molecular weights, can also be used.

The amount of a nanoparticle described herein that is effective for treating disorder or disease is determined using standard clinical techniques known to those with skill in the art. In addition, in vitro or in vivo assays can optionally be employed to help identify optimal dosage ranges. The precise dose to be employed can also depend on the route of administration, the condition, the seriousness of the condition being treated, as well as various physical factors related to the individual being treated, and can be decided according to the judgment of a health-care practitioner. For example, the dose of a nanoparticle described herein can each range from about 0.001 mg/kg to about 250 mg/kg of body weight per day, from about 1 mg/kg to about 250 mg/kg body weight per day, from about 1 mg/kg to about 50 mg/kg body weight per day, or from about 1 mg/kg to about 20 mg/kg of body weight per day. Equivalent dosages can be administered over various time periods including, but not limited to, about every 2 hr, about every 6 hr, about every 8 hr, about every 12 hr, about every 24 hr, about every 36 hr, about every 48 hr, about every 72 hr, about every week, about every 2 weeks, about every 3 weeks, about every month, and about every 2 months. The number and frequency of dosages corresponding to a completed course of therapy can be determined according to the judgment of a health-care practitioner.

In some instances, a pharmaceutical composition described herein is in unit dosage form, e.g., as a tablet, capsule, powder, solution, suspension, emulsion, granule, or suppository. In such form, the pharmaceutical composition can be sub-divided into unit doses containing appropriate quantities of a nanoparticle described herein. The unit dosage form can be a packaged pharmaceutical composition, for example, packeted powders, vials, ampoules, pre-filled syringes or sachets containing liquids. The unit dosage form can be, for example, a capsule or tablet itself, or it can be the appropriate number of any such compositions in package form. Such unit dosage form can contain from about 1 mg/kg to about 250 mg/kg, and can be given in a single dose or in two or more divided doses.

Combination Therapy

In some instances, a nanoparticle described herein is administered in combination with one or more therapeutic agents, e.g., therapeutic agents useful in the treatment of disorders or conditions described herein. For example, a nanoparticle that contains a chemotherapeutic agent can be administered in combination with a naked chemotherapeutic agent (i.e., not encapsulated within a nanoparticle).

Kits

A nanoparticle described herein can be provided in a kit. In some instances, the kit includes (a) a container that contains a nanoparticle and, optionally (b) informational material. The informational material can be descriptive, instructional, marketing or other material that relates to the methods described herein and/or the use of the nanoparticles, e.g., for therapeutic benefit.

The informational material of the kits is not limited in its form. In some instances, the informational material can include information about production of the nanoparticle, molecular weight of the nanoparticle, concentration, date of expiration, batch or production site information, and so forth. In other situations, the informational material relates to methods of administering the nanoparticles, e.g., in a suitable amount, manner, or mode of administration (e.g., a dose, dosage form, or mode of administration described herein). The method can be a method of treating a subject having a disorder.

In some cases, the informational material, e.g., instructions, is provided in printed matter, e.g., a printed text, drawing, and/or photograph, e.g., a label or printed sheet. The informational material can also be provided in other formats, such as Braille, computer readable material, video recording, or audio recording. In other instances, the informational material of the kit is contact information, e.g., a physical address, email address, website, or telephone number, where a user of the kit can obtain substantive information about the nanoparticles therein and/or their use in the methods described herein. Of course, the informational material can also be provided in any combination of formats.

In addition to the nanoparticles, the kit can include other ingredients, such as a solvent or buffer, a stabilizer, or a preservative. The kit can also include other agents, e.g., a second or third agent, e.g., other therapeutic agents. The components can be provided in any form, e.g., liquid, dried or lyophilized form. The components can be substantially pure (although they can be combined together or delivered separate from one another) and/or sterile. When the components are provided in a liquid solution, the liquid solution can be an aqueous solution, such as a sterile aqueous solution. When the components are provided as a dried form, reconstitution generally is by the addition of a suitable solvent. The solvent, e.g., sterile water or buffer, can optionally be provided in the kit.

The kit can include one or more containers for the nanoparticles or other agents. In some cases, the kit contains separate containers, dividers or compartments for the nanoparticles and informational material. For example, the nanoparticles can be contained in a bottle, vial, or syringe, and the informational material can be contained in a plastic sleeve or packet. In other situations, the separate elements of the kit are contained within a single, undivided container. For example, the nanoparticles can be contained in a bottle, vial or syringe that has attached thereto the informational material in the form of a label. In some cases, the kit can include a plurality (e.g., a pack) of individual containers, each containing one or more unit dosage forms (e.g., a dosage form described herein) of the nanoparticles. The containers can include a unit dosage, e.g., a unit that includes the nanoparticles. For example, the kit can include a plurality of syringes, ampules, foil packets, blister packs, or medical devices, e.g., each containing a unit dose. The containers of the kits can be air tight, waterproof (e.g., impermeable to changes in moisture or evaporation), and/or light-tight.

The kit can optionally include a device suitable for administration of the nanoparticles, e.g., a syringe or other suitable delivery device. The device can be provided pre-loaded with nanoparticles, e.g., in a unit dose, or can be empty, but suitable for loading.

The invention is further described in the following examples, which do not limit the scope of the invention described in the claims.

EXAMPLES

Example 1

Inhibition of (MDR1) Expression by an siRNA Nanoparticle Delivery System to Overcome Drug Resistance in Osteosarcoma A novel drug delivery system was constructed and evaluated for MDR1 siRNA delivery. Novel biocompatible, lipid-modified dextran-based polymeric nanoparticles were used as the platform for MDR1 siRNA delivery, and the efficacy of combination therapy with this system was evaluated.

A. Materials and Methods

Chemicals

Dextran (Mw about 40 kDa), stearyl amine (99% pure), cystamine, pyridine, sodium periodate (NaIO$_4$), sodium cyanoborohydride (NaCNBH$_3$), potassium sulfate (K$_2$SO$_4$) and azo-bis-isobutyronitrile (AIBN) were obtained from Sigma-Aldrich Chemical Co (St. Louis, Mo.). Dithiol-modified poly(ethylene glycol) (PEG-(SH)$_2$, M.W. 2,000) was purchased from SunBio, Inc. (Seoul, South Korea) Anhydrous lithium chloride (LiCl) was obtained from Fisher Scientific (Philadelphia, Pa.). Dehydrated dimethylformamide (DMF) and dimethylsulfoxide (DMSO) with molecular sieves were obtained from Acros Organics (Parsipanny, N.J.). Acryloyl chloride, pyridine and other reagents and solvents were from Sigma-Aldrich and were used as received without further purification.

Synthesis of ABCB1 siRNA

The siRNA sequence targeting the ABCB1 gene (Genbank accession no. NM_000927) corresponded to its coding region of this gene. Four target sequences were selected for the ABCB1 gene. Sense sequences for each siRNA were 5' GAG CUUAACA CC CGA CUUAUU 3' (SEQ ID NO: 1), 5' GAAAGUAUACCUCCAGUUUUU 3' (SEQ ID NO: 2), 5' GAC CAUAAAU GUAAGGUUUUU 3' (SEQ ID NO: 3), and 5' CCAGGUAUGCCUAUUAUUAUU 3' (SEQ ID NO: 4).

Synthetic siRNA duplexes were obtained from Dharmacon Inc. (Layfayette, Colo.). The siRNAs were dissolved by adding 1 mL of the buffer (100 mmol/L potassium acetate, 30 mmol/L HEPES-KOH, and 2 mmol/L magnesium acetate (pH 7.4)) to each tube, and stored at −20° C. until the following transfection method.

Synthesis of Dextran Acrylate

The synthesis of dextran acrylate was based on the procedure of Zang et al., *J. Polym. Sci. Part A: Polym. Chem.* 41:386-394 (2003). Briefly, a fixed amount of dextran (M.W. about 40 kDa, 2 g) was added to a LiCl/DMF (4% w/v, 50 ml) solvent mixture in a round bottom flask (200 ml). The temperature of the oil bath was raised from room temperature (RT) to 120° C. over a period of 2 h. The resultant mixture became a homogeneous golden yellow colored solution. The solution was cooled to RT, and pyridine (500 µL) was added and stirred. The reaction mixture was cooled to 0° C. using ice bath, and varying amounts of acryloyl chloride (1-1.5 molar excess) were added drop wise using an addition funnel. The reaction was maintained at 0° C. until complete addition of acryloyl chloride was done over a period of 1-2 h. The reaction was allowed to continue overnight. The dextran-acrylate obtained was precipitated in excess cold ethanol and washed 3× with absolute ethanol. For confirmation of the formation of dextran acrylate, a small portion of the acrylate monomer was polymerized using 0.001% AIBN initiator in DMSO at 60° C. for 24 hr, which resulted in formation of the acrylate polymer, confirming the reaction. Alternately, for lipid modification, the dextran-acrylate was directly used as the monomer for the next step, in a one-pot synthesis.

Figure 5A:
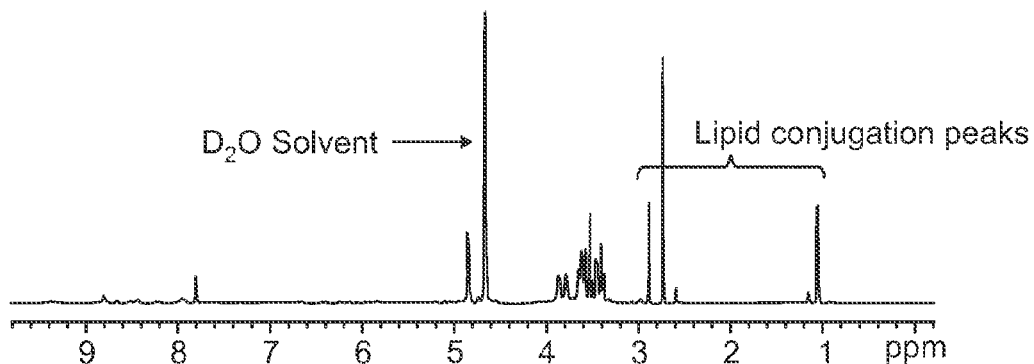
FIG. 5A is a graphic representation of a 500 MHz 1H NMR spectrum of dextran.
Figure 5B:
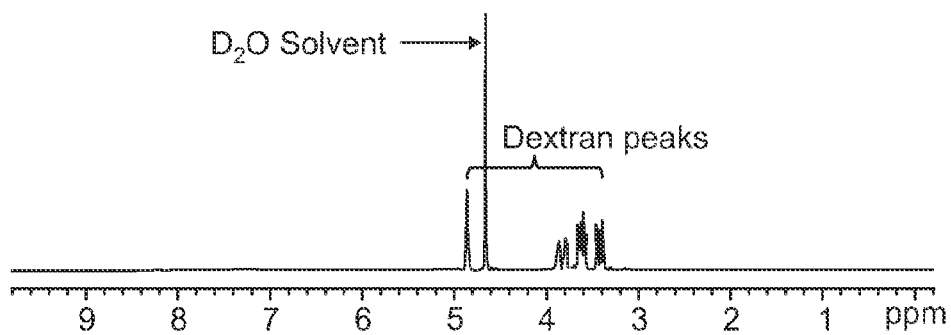
FIG. 5B is a graphic representation of a 500 MHz 1H NMR spectrum of dextran conjugated stearyl amine after purification.

Lipid Modification of Dextran Acrylate 200 mg of dextran acrylate obtained from above step was dissolved in dry DMF and stirred in a 20 mL glass vial with varying amounts (5-10 mole %) of stearylamine and a catalyst (0.01 mole % AlCl$_3$). The reaction mixture was heated to 40-50° C. in an oil bath for 24 h. The product obtained (stearylamine-modified dextran) was precipitated and washed in cold ethanol several times to purify the product. The lipid-modified dextran derivative was then dissolved in small amount of deionized water and lyophilized to yield the pale yellow colored final product. The fatty amine modification of dextran was confirmed by 1H NMR spectroscopy (Varian 500 MHz NMR spectrometer, Varian Inc, CA) and the % lipid modification was estimated to be 7 mole %. FIG. 5 shows the resulting spectra (where D$_2$O was used as the solvent) having the additional peaks of the long chain fatty amine at about 1 ppm indicating the successful lipid modification of dextran. The % fat modification was estimated to be 7 mole % of dextran.

Other derivatives of different blocks and their combination that were synthesized are shown in Table 2.

TABLE 2

| Hydrogel/hydrophilic backbone | Hydrophobic group | Thiol containing linker |
|---|---|---|
| Dextran (Av Mw 40 kDa) | Butyl amine | Cystamine |
| Dextran (Av Mw 80 kDa) | Hexyl amine | 2-immuno thiolane |
| | Oleyl amine | Cystamine hydrochloride |
| | Lauryl amine | 2,2'-dithiopyridine |
| | Stearyl amine | |
| | Dodecyl amine | |

Oxidation of Dextran

Dextran is an α-D-1,6-glucose-linked glucan with side chains 1-3 linked to the backbone units of the dextran biopolymer. Dextran was selected for the development of the macrostructure based on its long history of use as plasma expander and drug delivery platform. The dextran backbone was oxidized based on the procedure of Surangkhana et al., *Langmuir* 22:8192-8196 (2006). Briefly, a desired amount of $NaIO_4$ was dissolved in 60 mL of deionized water. The solution was added to another solution containing 4 g of dextran and 30 mL of de-ionized water. The reaction was stirred in the dark for 2 h at RT. At the end of the reaction, the solution was dialyzed using Spectrapor® dialysis membranes (M.W. cut-off 12-14 kDa, Spectrum Labs, Rancho Dominguez, Calif.) against de-ionized water (2 L) for 4 days with several water replacements. A powdery free-flowing sample was obtained after freeze-drying, yielding 3.7 g (92.5%).

Thiol Modification of Dextran

A 500 mg portion of the oxidized dextran was dissolved in 50 mL pH 5.2 buffer containing $K_2SO_4$ and $NaCNBH_3$. 50 mg of cystamine was added and stirred at 40° C. for 4 days. The product was subjected to extensive dialysis and then lyophilized to yield thiolated dextran. The % thiolation was quantified by Ellman's reagent (Ellman, *Arch. Biochem. Biophys.* 82:70-77 (1959)). The concentration of sulfohydryl groups in the purified thiolated dextran derivate was estimated to be about 14.2 μM/mg.

Preparation of MDR1 siRNA-Containing Dextran Nanoparticles

A stock solution of 5 mg/mL PEG-$(SH)_2$, stearylamine-modified dextran, and thiolated dextran (synthesized as described above) was prepared in deionized water. To a solution of MDR1 siRNA, 40 μL of dextran-thiol was first added and mixed well using a vortex shaker. It was then incubated for 5 min. To this mixture, 40 μL, dextran-stearylamine derivative was then added and incubated for another 5 min. Finally, 40 μL of PEG-$(SH)_2$ was added and incubated for another 15 min to form the hydrophilic shell of the nanoparticles. This method of sequential addition was used to result in better interaction between the siRNA, the thiol, and the lipid modified dextran derivatives; to provide stealth character to the nanoparticle, a shell of PEG-thiol was added.

Particle Size and Zeta Potential Measurements

The particle size and zeta potentials of MDR1 siRNA-loaded nanoparticles were performed with a Brookhaven Zeta PALS Instrument (Holtsville, N.Y.). For light scattering experiments, the samples were measured at fixed angle of 90° at 25° C. The scattering intensity was adjusted in the range of 50-500 kcps by diluting the samples with deionized water. For zeta potentials, default parameters of dielectric constant, refractive index, and viscosity of water were used based on the electrophoretic mobility of the nanoparticles.

Cell Culture and Reagents

The human osteosarcoma cell line KHOS and the multi-drug-resistant MDR1 (P-gp) expressing cell lines $KHOS_{R2}$ and $U-2OS_{R2}$ were obtained from the National Hellenic Research Foundation, Athens, Greece. All cell lines were cultured in RPMI 1640 medium supplemented with 10% fetal bovine serum, 100 U/mL penicillin, and 100 μg/mL streptomycin (all obtained from Invitrogen, Carlsbad, Calif.). Cells were incubated at 37° C. in 5% $CO_2$-95% air atmosphere and passaged when near confluent monolayers were achieved using trypsin-EDTA solution. Resistant cell lines were continuously cultured in doxorubicin. Doxorubicin was obtained from the Sigma-Aldrich (St. Louis, Mo.). The P-gp1 monoclonal antibody C219 was purchased from Signet (Dedham, Mass.). The human β-actin monoclonal antibody and the MTT reagents were purchased from Sigma-Aldrich (St. Louis, Mo.).

Generation of EGFP-Expressing Cells and Transfection by EGFP siRNA-Loaded Nanoparticles The Stat3 and enhanced green fluorescent protein (EGFP) fusion protein expression vector pCORON1000 EGFP-Stat3 (pEGFP-Stat3) was obtained from Amersham Biosciences (Buckinghamshire, UK). This pEGFP-Stat3 vector was generated by fusing Stat3 to the COOH terminus of EGFP. A hamster kidney cell line (BHK-21) was stably transfected with pEGFP-Stat3 through selection with G418 (Invitrogen, Carlsbad, Calif.). EGFP expressing cells were seeded at a density of about 4000 cells per well in 96-well plates with addition of increased concentration of EGFP siRNA and subsequently incubated for 48 hr. EGFP siRNA was obtained from Ambion (Austin, Tex.). siPORTT™ NeoFX™ Transfection Agent was used as a positive control (Ambion). Images were acquired by Nikon Eclipse Ti-U fluorescence microscope (Nikon Corp.) equipped with a SPOT RT digital camera (Diagnostic Instruments, Inc., Sterling Heights, Mich.).

Western Blot Analysis

P-gp1 was analyzed in total cell lysates. Protein lysates from cells were generated through lysis with 1×RIPA Lysis Buffer (Upstate Biotechnology, Charlottesville, Va.). The concentration of the protein was determined by Protein Assay reagents (Bio-Rad, Hercules, Calif.) and a spectrophotometer (Beckman DU-640, Beckman Instruments, Inc., Columbia, Md.). 25 μg of total protein was processed on Nu-Page 4-12% Bis-Tris Gel (Invitrogen) and transferred to a pure nitrocellulose membrane (Bio-Rad Laboratories, Hecules, Calif.). Primary antibodies were incubated in Tris-buffered saline, pH 7.4, with 0.1% Tween 20 overnight at 4° C. Signal was generated through incubation with horseradish peroxidase-conjugated secondary antibodies (Bio-Rad, Hercules, Calif.) incubated in Tris-buffered saline, pH 7.4, with 5% nonfat milk and 0.1% Tween 20 at 1:2000 dilution for 1 h at RT. Positive immunoreactions were detected by using Super Signal West Pico Chemiluminescent Substrate (Pierce, Rockford, Ill.). Bands were semi-quantified by reverse image scanning densitometry with PhotoShop 7.0 (Adobe, San Jose, Calif.). An area of the gel image that was devoid of signal was assigned to be the background value. Then each band of the protein representing P-gp from $KHOS_{R2}$ or $U2OS_{R2}$ treated with various concentrations of MDR1 siRNA nanoparticles was analyzed for density beyond the background level. To ensure that the loading of the protein was equal and differences were not being observed because of one specimen having more protein than another, the band corresponding to β-actin was determined for each protein. The density of the protein band was normalized to the β-actin band for the protein and the ratio of the P-gp was normalized by dividing by the ratio of the β-actin corresponding to each P-gp.

Duration of MDR1 Reversal

For comparison of the duration of MDR1 inhibition by either MDR1 siRNA, alone, or MDR1 siRNA-loaded nanoparticles, $1\times10^5$ $KHOS_{R2}$ cells/well were incubated with MDR1 siRNA, alone, and in nanoparticle form for 5 days. The expression of P-gp was determined by western blot analysis as described above.

Drug Efflux Assay

The Vybrant™ multi-drug resistance assay kit (Invitrogen/Molecular Probes) was used to measure the drug efflux properties of the resistant cell lines. This assay utilizes the fluorogenic dye calcein acetoxymethyl ester (calcein AM) as a substrate for efflux activity of P-gp or other membrane pump ABC proteins. Calcein AM is taken up by cells and hydrolyzed by cytoplasmic esterases into fluorescent calcein. Calcein AM is well retained in the cytosol. However, multidrug-resistant cells expressing high levels of P-gp rapidly extrude non-fluorescent calcein AM from the plasma membrane, reducing accumulation of fluorescent calcein in the cytosol. Drug-resistant cells ($1 \times 10^5$) were cultured in 96-well plates with either increasing concentrations of MDR1 siRNA-loaded nanoparticles or with media, alone. After 48 hr, the cells were incubated with 0.25 μM calcein AM in 150 μL total volume. 10 μM Verapamil was used as a positive control and PBS as a negative control. After 30 min, the cells were washed and centrifuged twice with 200 μL cold RPMI1640 culture medium, and cell fluorescence was measured at a wavelength of 490 nm ($A_{490}$) on a SPECTRAmax® Microplate Spectrofluorometer (Molecular Devices). For visualization of the intracellular retention of calcein AM, images were acquired by Nikon Eclipse Ti-U fluorescence microscope (Nikon Corp.) equipped with a SPOT RT digital camera (Diagnostic Instruments, Inc., Sterling Heights, Mich.).

Fluorescence Microscopy of Cellular Doxorubicin Uptake

For cellular uptake studies, KHOS and $KHOS_{R2}$ cells were seeded at densities of $5 \times 10^5$ cells/well in 6 well plates. MDR1 siRNA was applied to a well of $KHOS_{R2}$ and incubated for 48 h. Following the incubation, doxorubicin was added to each well and was incubated for additional 3 hr. After incubation, the cells were washed, suspended in fresh RPMI 1640, then visualized on a Nikon Eclipse Ti-U fluorescence microscope equipped with a SPOT RT digital camera (Diagnostic Instruments, Inc., Sterling Heights, Mich.). Fluorescence intensity and cellular localization was analyzed at a wavelength of 488 nm in triplicate in random, different fields.

In Vitro Cytotoxicity Assay

In vitro cytotoxicity assays were performed by MTT assay as previously described. Briefly, $3 \times 10^3$ cells per well were plated in a 96-well plate during this process. After 48 hr of incubation with MDR1 siRNA-loaded nanocarriers or with medium alone, increasing concentrations of doxorubicin were applied. After culturing for 5 days, 10 μL of MTT (5 mg/mL in PBS) was added to each well and incubated for 3 hr. After dissolving the resulting formazan product with acid isopropanol, the absorbance ($A_{490}$) was read on a SPECTRA max Microplate Spectrophotometer (Molecular Devices) at a wavelength of 490 nm. Each experiment was performed in triplicate.

Statistical Analysis

Student's t-test was used to compare the differences between groups (GraphPad PRISM® 4 software, GraphPad Software, San Diego, Calif.). Results were given as mean±SD and results with $p<0.05$ were considered statistically significant.

B. Results

Lipid-Modified Dextran Nanoparticles for Intracellular MDR1 siRNA Delivery

For preparation of MDR1 siRNA-loaded nanoparticles, MDR1 siRNA was incubated with the thiol-modified dextran derivative in deionized water at RT to form nanoparticles by thiol-amine association between the thiolated dextran derivative and the free amines on the siRNA (Sainsbury et al., J. Phys. Chem. 111:12992-12999 (2007)). Furthermore, a stearylamine modified dextran derivative and a PEGylated-thiol derivative was sequentially mixed with the siRNA containing thiol-dextran derivate to form a hydrogel network to enhance the binding efficiency and stability of PEG chains to the ternary network. This method resulted in the formation of stable nanoparticles with good siRNA-loading and binding of PEG chains (FIG. 6). The mean particle size of the MDR1 siRNA-loaded nanoparticles as determined by dynamic light scattering (DLS) measurement was 104.4+3.7 nm and the zeta potential was almost neutral (−0.19+1.13 mV). Tables 3 and 4 show the particle sizes and zeta potentials for other polymers.

TABLE 3

Particle Size and Zeta Potential of Dextran-Acrylate-Lipid Modified Polymers

| Polymer | Mean Particle size (nm) | Poly-dispersity | Zeta potential (mV) |
| --- | --- | --- | --- |
| Dextran 40 kDa | 32.8 ± 1.9 | 0.320 | −1.96 ± 0.74 |
| Dextran 80 kDa | 18.4 ± 0.5 | 0.277 | −14.76 ± 1.92 |
| Dextran-butyamine (C4) | 430.4 ± 19.7 | 0.341 | +2.17 ± 0.83 |
| Dextran-hexylamine (C6) | 220 ± 6.3 | 0.34 | +2.49 ± 0.54 |
| Dextran-dodecylamine (C12) | 419.2 ± 34.8 | 0.415 | +7.11 ± 1.78 |
| Dextran-octadecylamine (C18) | 234.8 ± 3.5 | 0.137 | +36.6 ± 2.55 |

TABLE 4

| Polymer sample | Mean Nm particle size | Poly-dispersity | Zetapotential (mV) |
| --- | --- | --- | --- |
| Dextran-thiol | 67 ± 16.9 | 0.770 | −6.08 ± 3.62 |
| Dex-Butyl amine + Dex-thiol (1:1) | 104.4 ± 34.7 | 0.629 | −0.19 ± 1.13 |
| Dex-Hexyl amine + Dex-thiol | 93.3 ± 20.3 | 0.937 | 18.65 ± 1.51 |
| Dex-Oleyl amine + Dex-thiol | 68.4 ± 26.8 | 0.556 | 11.18 ± 2.81 |
| Dex-Dodecyl amine + Dex-thiol | 109.6 ± 30.2 | 0.978 | 0.00 |
| Dex-stearylamine + Dex-thiol | 386.7 ± 18.6 | 0.421 | 13.5 ± 2.45 |

The particles were stable at RT and there was minimal change in the particle size upon storage (at least for 1 week at 4° C.).

Figure 4:
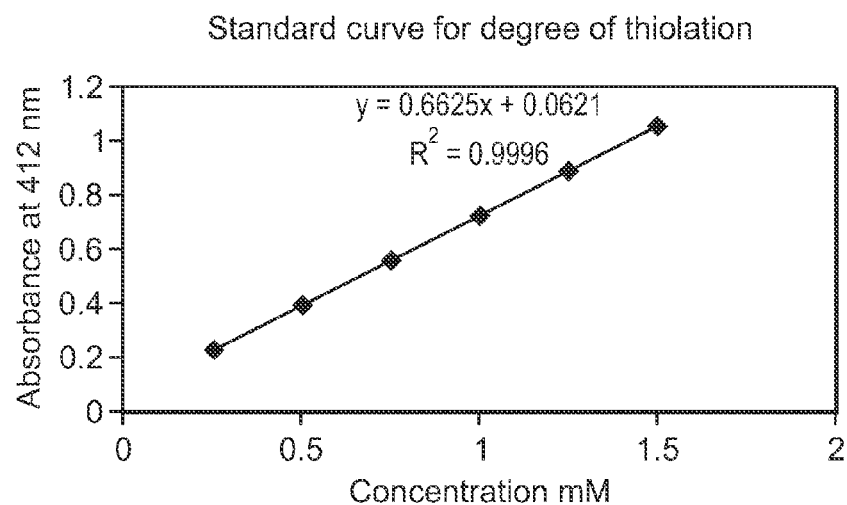
FIG. 4 is a graphic representation of degree of thiolation of dextran.

The concentration of sulphohydrl groups in the purified thiolated dextrans (40 kDa and 80 kDa) were 14.2 μM/mg and 11.2 μM/mg, respectively. The results are shown in FIG. 4.

Effect of EGFP siRNA-Loaded Nanoparticle on BHK-21-EGFP Cells

Figure 8:
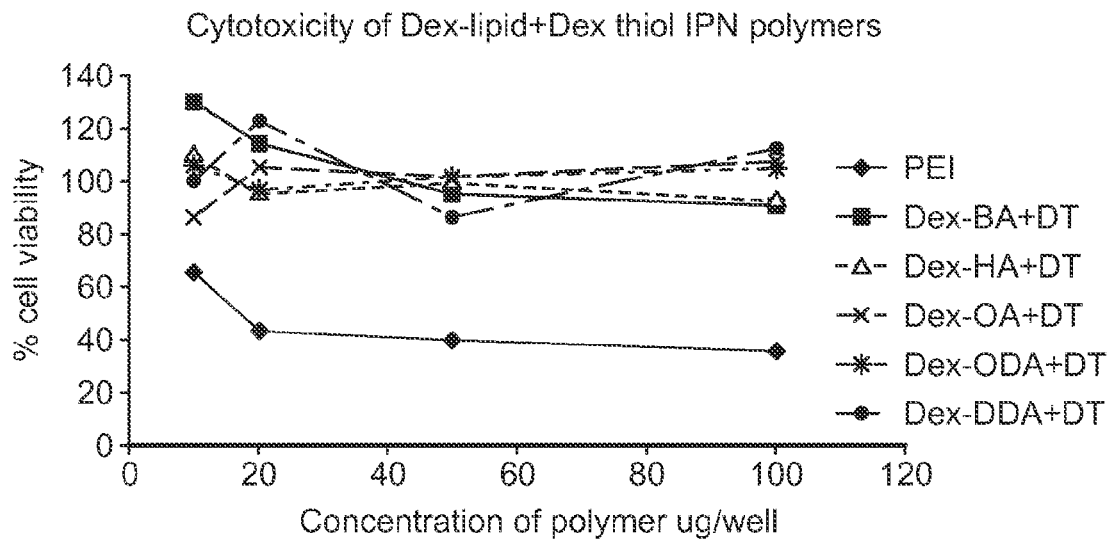
FIG. 8 is a graphic representation of cytotoxicity of thiolated polymers. Cytotoxicity was measured by incubating different concentrations of the polymeric derivatives with SKOV3 ovarian cancer cells. The relative cell viability (in percent) was determined by the formazan (MTT) assay.
Figure 9:
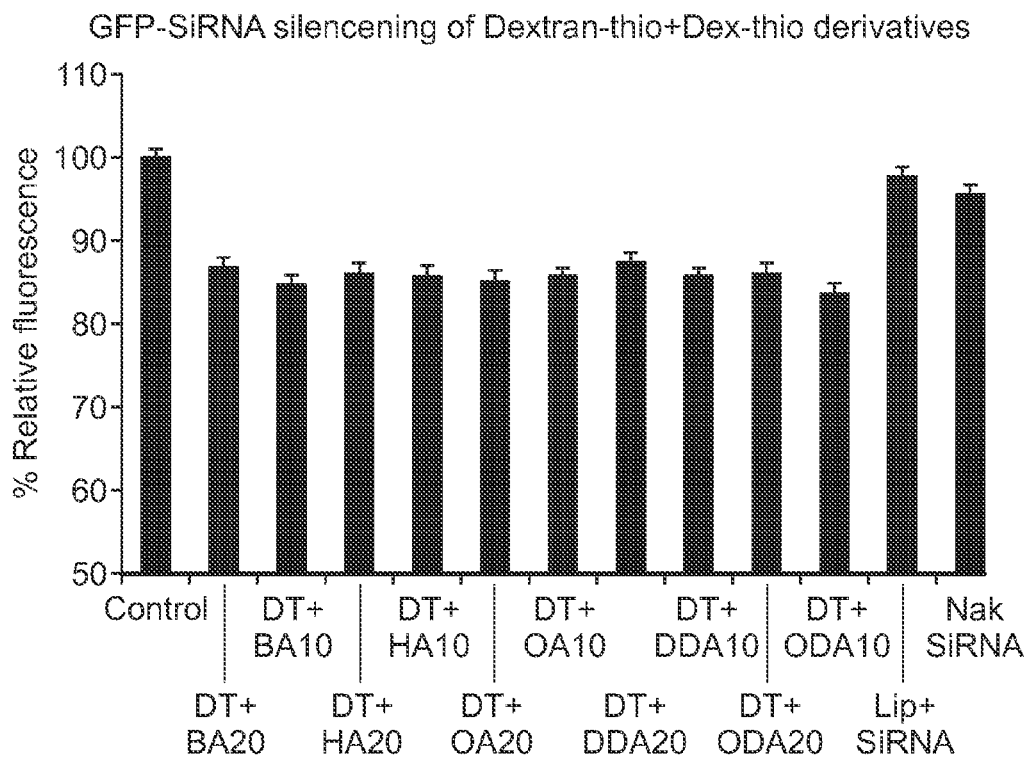
FIG. 9 is a graphic representation of GFP-siRNA silencing of thiolated dextran derivatives.

To assess the transfection efficacy of siRNA-loaded nanoparticles on cell lines, we first utilized EGFP expressing BHK-21 cells to test the effects. The EGFP siRNA-loaded nanoparticles were non-toxic at the concentrations utilized in this study, as shown in FIGS. 7 and 8. The EGFP siRNA was efficiently incorporated into cells and effectively inhibited the expression of EGFP (FIG. 9). The inhibition was dose dependent, but reached a plateau at approximately 100 nm.

To assess the inhibition of other nanoparticles, 10 μg of the predissolved polymer (Dex-thio+Dex lipid) were incubated with 150 nm of GFP-SiRNA for 30 min. The silencing effect was studied after 24 h incubation with BHKpEGFP cells in 96-well plates. The results are shown in FIG. 9.

The cytotoxicity of these derivatives was tested on SKOV3 ovarian cancer cells relative to PEI positive controls. The results are shown in FIGS. 7 and 8. The mixture of dextran derivatives (thiol+lipid) was found to be relatively non-toxic at the tested concentration relative to PEI.

Stable Suppression of P-gp Using MDR1 siRNA-Loaded Nanoparticle

Figure 10A:
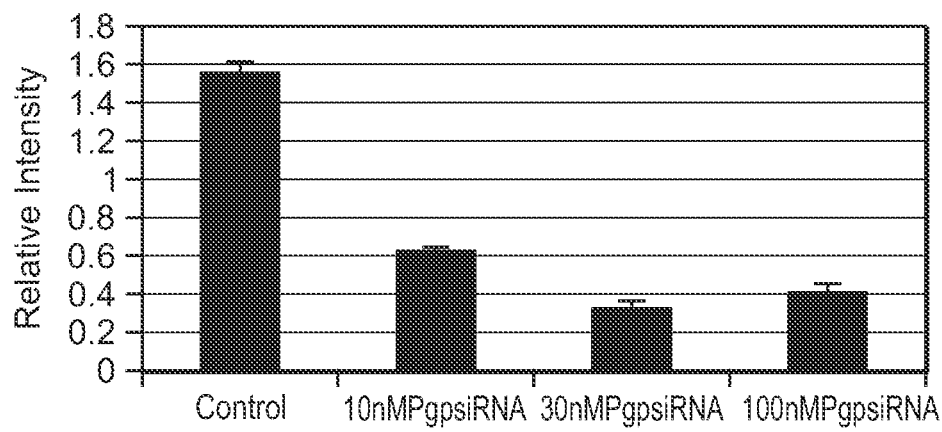
FIG. 10A is a graphic representation of a Western blot analysis of P-gp expression in $KHOS_{R2}$ cells following treatment with MDR1 siRNA-loaded nanoparticles.
Figure 10B:
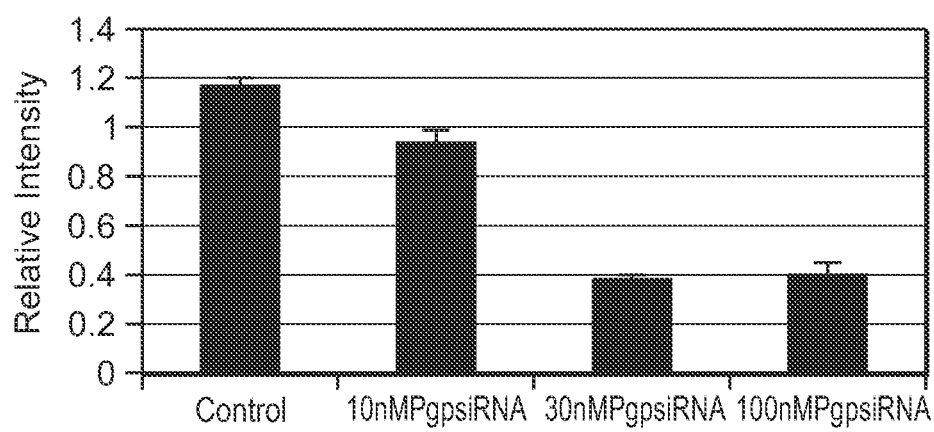
FIG. 10B is a graphic representation of a Western blot analysis of P-gp expression in $U-2OS_{R2}$ cells following treatment with MDR1 siRNA-loaded nanoparticles.
Figure 11A:
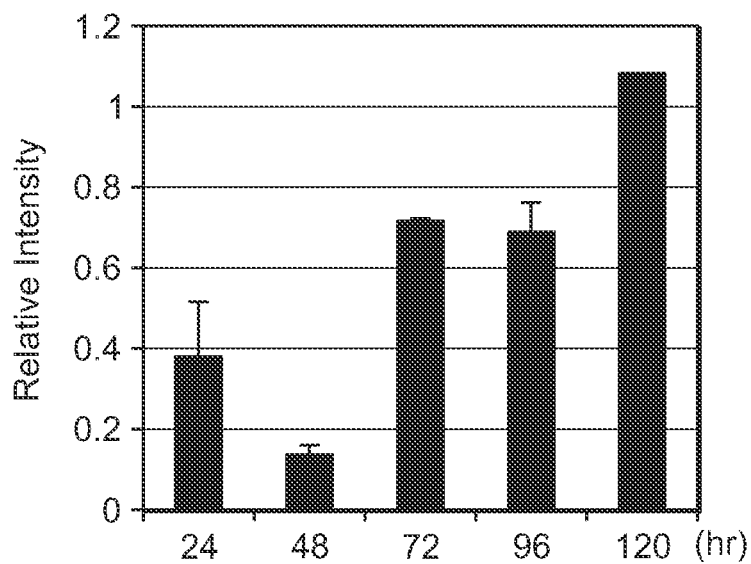
FIG. 11A is a graphic representation of a Western blot analysis of P-gp expression in $KHOS_{R2}$ cells following treatment with naked MDR1 siRNA.
Figure 11B:
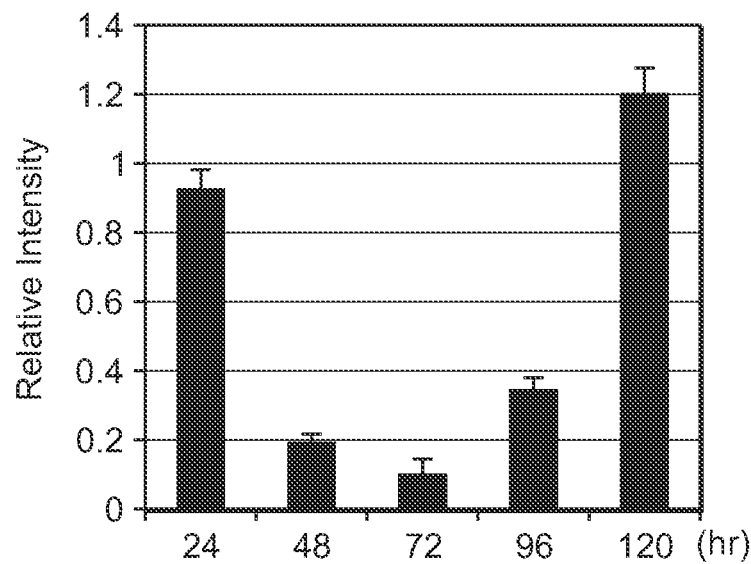
FIG. 11B is a graphic representation of a Western blot analysis of P-gp expression in $KHOS_{R2}$ cells following treatment with MDR1 siRNA-loaded nanoparticles.

Western blotting was performed to estimate the effect of MDR1 siRNA-loaded nanoparticle on P-gp expression. P-gp expression was confirmed in the two drug-resistant cell lines $KHOS_{R2}$ and $U-2OS_{R2}$. MDR1 siRNA-loaded nanoparticle inhibited the expression of P-gp at a concentration of as low as 30 nM. The same effect was observed in two different drug-resistant osteosarcoma cell lines (FIGS. 10A and 10B). Naked siRNA was able to suppress P-gp expression for 48 hr. siRNA-loaded nanoparticles were slower in achieving the suppression of P-gp, but were able to maintain suppression for 96 hr (FIGS. 11A and 11B).

MDR1 siRNA-Loaded Nanoparticle Inhibits P-gp-Mediated Efflux of Calcein AM

Figure 12:
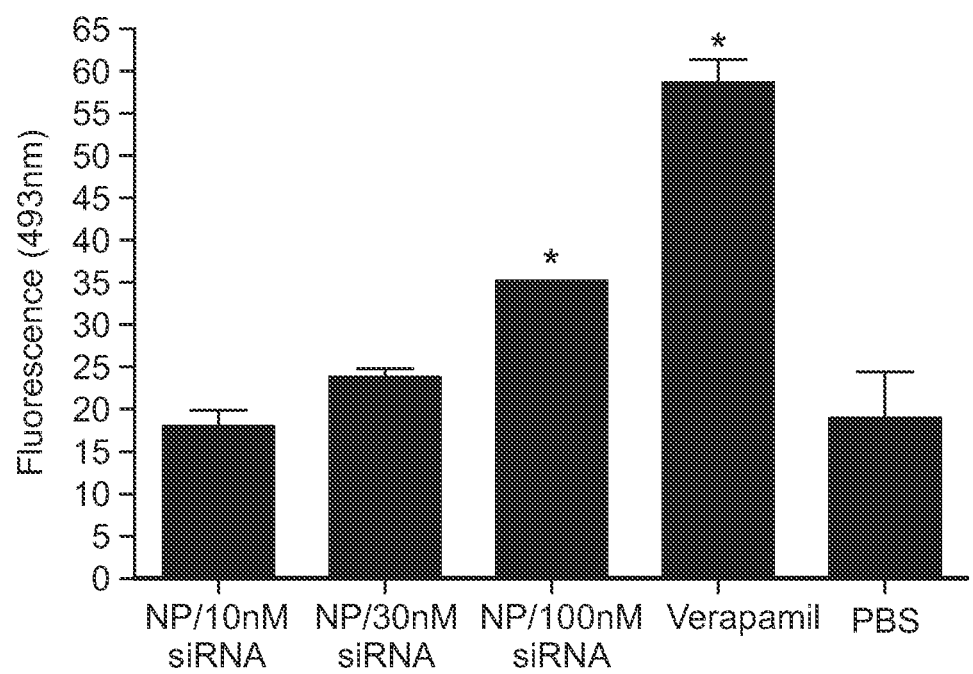
FIG. 12 is a graphic representation of P-gp-mediated uptake and efflux following treatment with MDR1 siRNA-loaded nanoparticle assessed using calcein AM.

Reversal of MDR is usually manifested as an increased intracellular accumulation of chemotherapeutics, which can be achieved by disturbing P-gp-mediated drug uptake and efflux. Therefore, the effect of MDR1 siRNA-loaded nanoparticles was examined for the uptake and efflux of a P-gp substrate, calcein AM, in $KHOS_{R2}$. Cells treated with MDR1 siRNA were shown to decrease calcein AM efflux in a dose-dependent manner as determined by image analysis, and confirmed by microplate spectrofluorometer analysis (FIG. 12).

Enhancement of Intracellular Doxorubicin Accumulation with MDR1 siRNA-Loaded Nanoparticle Delivery Using fluorescent microscopy, subcellular distribution of doxorubicin in KHOS and $KHOS_{R2}$ was analyzed. After a 3 hr incubation period with free doxorubicin in drug-resistant osteosarcoma cells, the drug was primarily concentrated in the cytoplasm with a very low level of fluorescence observed in the nucleus. When doxorubicin was administered after treatment with MDR1 siRNA-loaded nanoparticle to drug-resistant cell lines, an increase in fluorescence was observed in the nucleus and cytoplasm. This subcellular distribution mimicked that of the drug sensitive variant when treated with doxorubicin.

In Vitro Cytotoxicity Studies in Drug-Resistant Osteosarcoma Cells

Figure 13A:
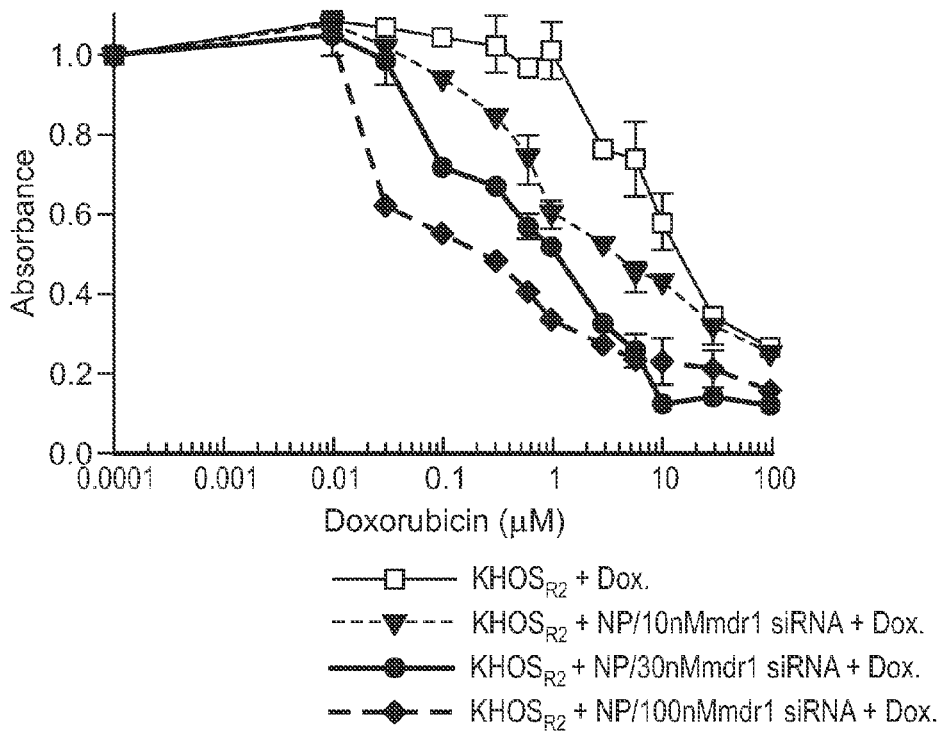
FIG. 13A is a graphic representation of the effect of doxorubicin, alone, or nanoparticle-loaded with MDR1 siRNA on $KHOS_{R2}$ cells.
Figure 13B:
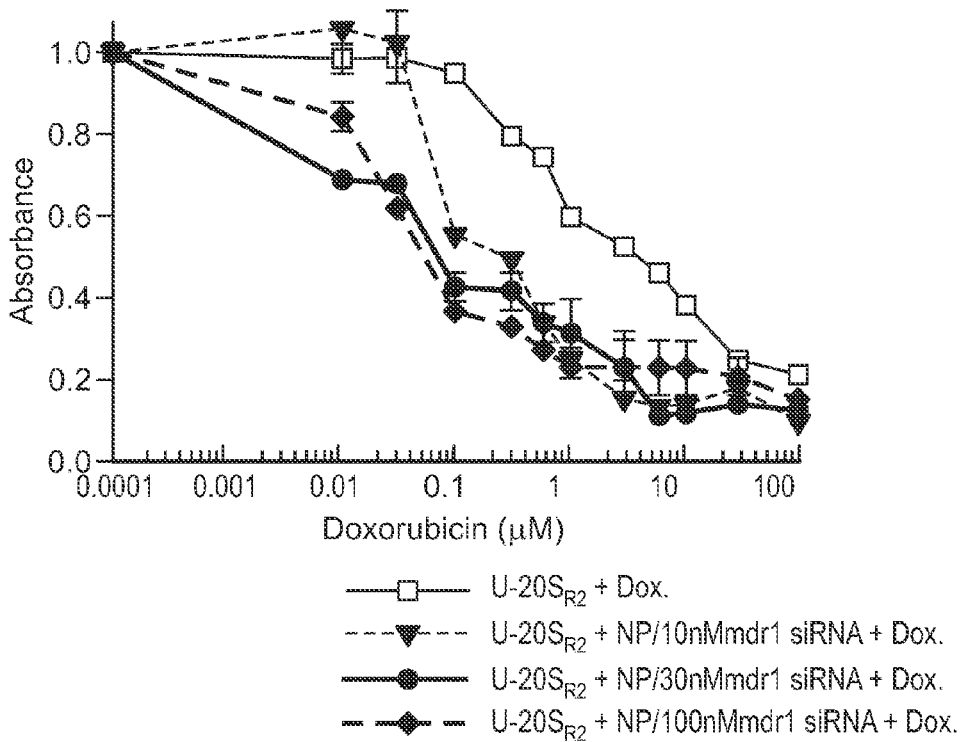
FIG. 13B is a graphic representation of the effect of doxorubicin, alone, or nanoparticle-loaded with MDR1 siRNA on $U-2OS_{R2}$ cells.

The dextran nanoparticles were not cytotoxic by themselves at the dose used. After treatment with MDR1 siRNA-loaded nanoparticles, doxorubicin showed an increased amount of anti-proliferative activity in drug-resistant osteosarcoma cell lines in a dose-dependent manner (FIGS. 13A and 13B). With the delivery of nanoparticles loaded with 100 nM MDR1 siRNA, growth inhibition with doxorubicin was substantially more marked than with the administration of 100-fold higher amounts of free drugs. For example, in the $KHOS_{R2}$ cell line, the $IC_{50}$ of doxorubicin, alone, was 10 μM, which was reduced to 0.1 μM when the cells were co-treated with MDR1 siRNA-loaded nanoparticles. Likewise, the drug-resistant cell line $U-2OS_{R2}$ displayed a similar trend; the $IC_{50}$ for doxorubicin, alone, was 6 μM, which was reduced to 0.06 μM when co-treated with the MDR1 siRNA-loaded nanoparticles.

In this Example, multi-drug-resistant osteosarcoma cell lines ($KHOS_{R2}$ and $U-2OS_{R2}$) were treated with the MDR1 siRNA nanocarriers and MDR1 protein (P-gp) expression, drug retention, and immunofluorescence were analyzed. Combination therapy of the MDR1 siRNA-loaded nanocarriers with increasing concentrations of doxorubicin was also analyzed. MDR1 siRNA-loaded dextran nanoparticles efficiently suppressed P-gp expression in drug-resistant osteosarcoma cell lines. The results also demonstrated that this approach can reverse drug resistance by increasing the amount of drug accumulation in MDR cell lines. Thus, lipid-modified dextran-based polymeric nanoparticles can be used as a platform for siRNA delivery. Further, nanocarriers loaded with MDR1 siRNA can be used as a treatment strategy for reversing MDR in osteosarcoma.

Example 2

Doxorubicin-Loaded Polymeric Nanoparticulate Delivery System to Overcome Drug Resistance in Osteosarcoma A. Materials and Methods Dextran (Mw about 40 kDa), stearyl amine (99% pure), cystamine, pyridine, sodium periodate ($NaIO_4$), sodium cyanoborohydride ($NaCNBH_3$), and potassium sulfate ($K_2SO_4$) and azo-bis-isobutyronitrile (AIBN) were obtained from Sigma-Aldrich Chemical Co (St. Louis, Mo.). Dithiol-modified poly(ethylene glycol) ($PEG-(SH)_2$, M.W. 2,000) was obtained from SunBio, Inc. (Seoul, South Korea) Anhydrous lithium chloride (LiCl) was obtained from Fisher Scientific (Philadelphia, Pa.). Dehydrated dimethylformamide (DMF) and dimethylsulfoxide (DMSO) with molecular sieves was obtained from Acros Organics (Parsipanny, N.J.). Acryloyl chloride, pyridine and other reagents and solvents were from Sigma-Aldrich and were used as received without further purification.

Lipid-modified dextran derivatives and thiolated dextran were prepared as described in Example 1.

Preparation of Doxorubicin-Containing Dextran Nanoparticles

A stock solution of 5 mg/mL $PEG-(SH)_2$, stearylamine-modified dextran, and thiolated-dextran synthesized above were prepared in deionized water. A 10 mM (1 mL) stock solution of doxorubicin was used for the preparation of doxorubicin-loaded nanoparticles. For preparation of mixture, 40 μL of dextran-stearyl amine was first added to a 35 μL (0.35 mM) solution of doxorubicin and mixed well using a vortex shaker. It was then incubated for 5 min. To this mixture, 40 μL dextran-thiol derivative was added and incubated for another 5 min. Finally, 40 μL of $PEG-(SH)_2$ was added and incubated for another 15 min to form the hydrophilic shell of the nanoparticles. This method of sequential addition was used to allow a better interaction between the hydrophobic groups in doxorubicin and the lipid-modified dextran derivatives. Since the volume of the sample was small, it was gently vortexed and no stirring was used. The doxorubicin efficiency and loading in the nanoparticles was determined by measuring the $A_{485}$ absorbance of known amount of sample corresponding to λmax of doxorubicin and comparing the values to a standard curve obtained by using a stock solution of doxorubicin. Particle size and zeta potential measurements were conducted as described in Example 1.

Cell Culture Studies

Human osteosarcoma cell line U-2OS was obtained from the American Type Tissue Collection (Rockville, Md.). The National Hellenic Research Foundation, Athens, Greece kindly provided the human osteosarcoma cell line KHOS, U-2OS and the multidrug-resistant cell lines $KHOS_{R2}$, $U-2OS_{R2}$. All cell lines were maintained as described in Example 1.

Cytotoxicity Assay

In vitro cytotoxicity assays were performed by MTT assay as described in Example 1.

Quantitative and Qualitative Evaluation of Doxorubicin Uptake in Cells

For flow cytometry, cell suspensions of KHOS, $KHOS_{R2}$, U-2OS, and $U-2OS_{R2}$ incubated with doxorubicin with or without nanoparticle for 1 hr at 37° C. were analyzed for the cellular fluorescence in a FACS Calibur flow cytometer (BD Biosciences, San Jose, Calif.) with data acquisition using CellQuest software. Doxorubicin is intrinsically fluorescent and can be excited with the 488-nm argon laser light (Krishan et al., *Cancer Res.* 45:1046-1051 (1985)). The cells were washed and re-suspended in PBS and fluorescence emission (above 530 nm), and forward angle light scatter were collected, amplified, and scaled to generate histograms. A minimum of 500,000 cells were analyzed for each histogram generated. Final doxorubicin concentration used was 10 µM.

Cellular uptake studies were based on the fluorescence microscopic procedures of Venne et al. (*Cancer Res.* 56:3626-3629 (1996)). KHOS and $KHOS_{R2}$ cells were seeded at densities of $5 \times 10^5$ cells/well in 6 well plates and incubated for 24 hr to allow cell attachment. Following the incubation, either doxorubicin, alone, or nanoparticle-loaded with doxorubicin was added to each well and were incubated for additional 3 hr. After incubation, the cells were washed and resuspended with PBS and were then visualized on a Nikon Eclipse Ti-U fluorescence microscope (Nikon Corp.) equipped with a SPOT RT digital camera (Diagnostic Instruments, Inc., Sterling Heights, Mich.). Fluorescence intensity and cellular localization was analyzed at a wavelength of 488 nm in triplicate different fields at random.

Cellular Apoptosis Assay

Whole-cell lysates were immunoblotted with specific antibodies to PARP (Cell Signaling Technology) and its cleavage products. Positive immunoreactions were detected using Super Signal® West Pico Chemiluminescent Substrate. Bands were semiquantified by reverse image scanning densitometry with PhotoShop 7.0 (Adobe, San Jose, Calif.). An area of the gel image that was devoid of signal was assigned to be the background value. Each band of the protein representing cleaved PARP from KHOS or $KHOS_{R2}$ treated with either doxorubicin, alone, or nanoparticle-loaded with doxorubicin at various concentrations, were analyzed for the density beyond background level. To ensure that the loading of the protein was equal and differences were not being observed because of one specimen having more protein than another, the band corresponding to β-actin was determined for each protein. The density of the protein band was normalized to the β-actin band for the protein and the ratio of the cleaved PARP was normalized by dividing by the ratio of the actin corresponding to each cleaved PARP. As a second parameter of apoptotic cell death, caspase-3/7 activity was measured in KHOS and $KHOS_{R2}$ after treatment with either doxorubicin, alone, or nanoparticle-loaded with doxorubicin by using Apo-ONE Homogenous caspase-3/7 system according to the manufacturer's instructions (Promega, Madison, Wis.). The intensity of the emitted fluorescence was determined at a wavelength of 521 nm with the use of a SPECTRAmax® Microplate Spectrofluorometer (Molecular Devices).

B. Results

Lipid-Modified Dextran Nanoparticles for Intracellular Doxorubicin Delivery

Figure 14:
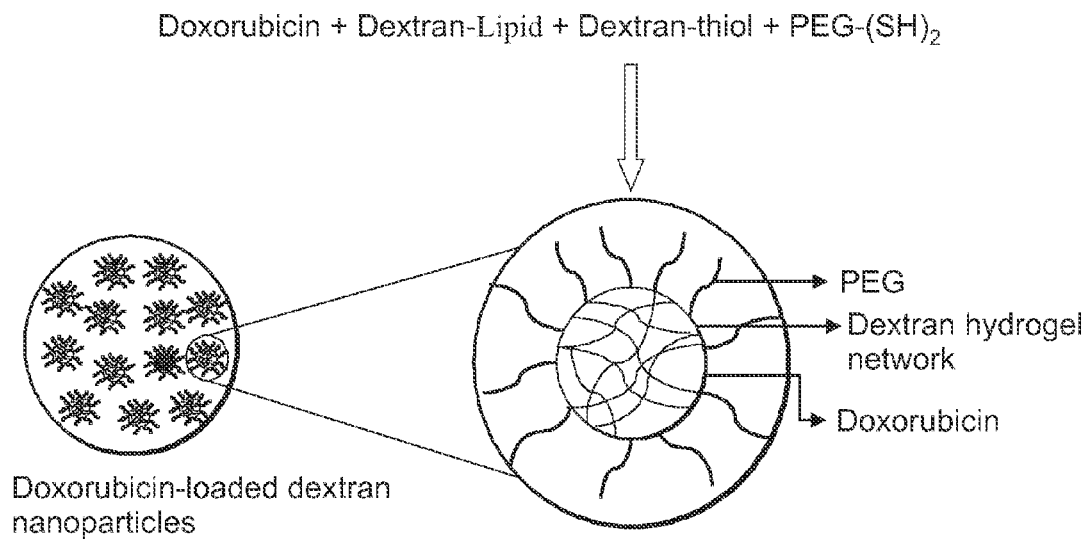
FIG. 14 is a schematic illustration of doxorubicin-loaded stearylamine-dextran modified nanoparticles.

Doxorubicin was incubated with the lipid-modified dextran derivative in deionized water at RT to form nanoparticles by self-assembled hydrophobic interactions. Further, a thiolated-dextran derivative and PEGylated-thiol derivative were sequentially mixed with the doxorubicin containing lipid-modified dextran derivatized to enhance the binding efficiency of PEG chains to the dextran hydrogel. This method resulted in the formation of stable nanoparticles with good doxorubicin loading (schematically depicted in FIG. 14). The mean particle size of the doxorubicin-loaded nanoparticles as determined by dynamic light scattering (DLS) measurement was 112.4±4.2 nm and the zeta potential was almost neutral (+1.19±0.82 mV). The particles were stable at RT and there was not much change in the particle size on storage (for 1 week at 4° C.).

Figure 15A:
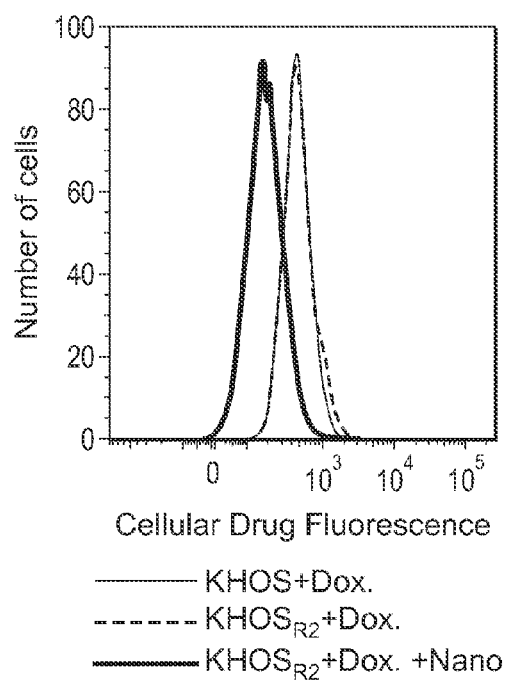
FIG. 15A is a graphic representation of fluorescence of KHOS and $KHOS_{R2}$ after treatment with doxorubicin, alone, or nanoparticle-loaded with doxorubicin analyzed by flow cytometry.
Figure 15B:
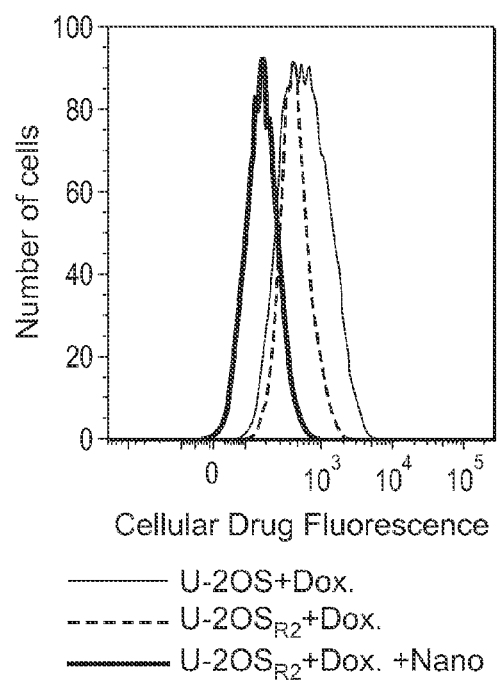
FIG. 15B is a graphic representation of fluorescence of U-2OS and $U-2OS_{R2}$ cells after treatment with doxorubicin, alone, or nanoparticle-loaded with doxorubicin analyzed by flow cytometry.

Enhancement of Intracellular Doxorubicin Accumulation with Nanoparticle Delivery Lipid-modified dextran nanoparticle caused a significant increase in the retention of doxorubicin in both $KHOS_{R2}$ (FIG. 15A) and $U-2OS_{R2}$ (FIG. 15B) when examined by flow cytometry. The fluorescence of drug-resistant cells treated with doxorubicin-loaded nanoparticles was comparable to that of drug sensitive cells treated with doxorubicin, alone.

Using fluorescent microscopy, subcellular distribution of doxorubicin in KHOS and $KHOS_{R2}$ was analyzed. After 3 hr incubation with free doxorubicin in drug-resistant osteosarcoma cells, the drug was primarily concentrated in the cytoplasm, and a very low level of fluorescence was observed in the nucleus. When doxorubicin was administered with the nanoparticle to drug-resistant cell line, a prominent increase in fluorescence was observed in the nucleus whereas the fluorescence of the cytoplasm remained virtually unaffected. This subcellular distribution mimicked that of the drug sensitive variant when treated with doxorubicin.

Evaluation of Anti-Proliferative Effects in Wild-type and Resistant Cells

Figure 16:
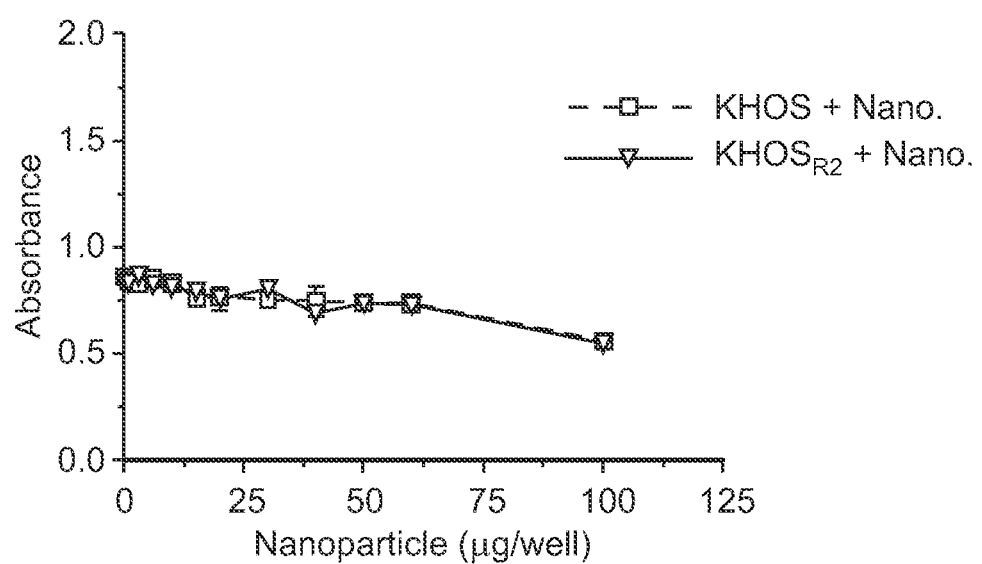
FIG. 16 is a graphic representation of the cytotoxicity of dextran nanoparticles on KHOS and $KHOS_{R2}$ cells.
Figures 17A, 17B:
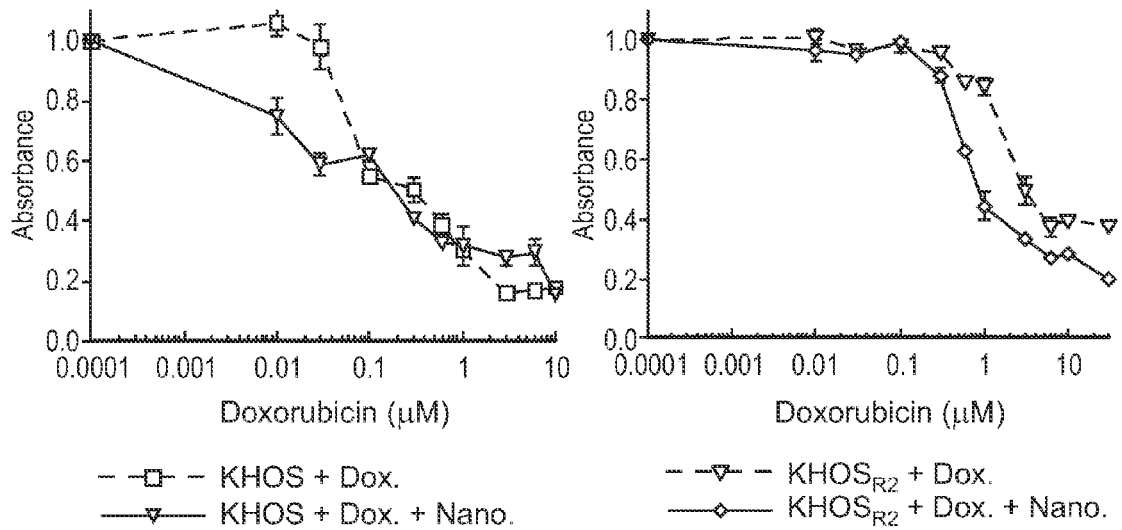
FIG. 17A is a graphic representation of the anti-proliferative activity of doxorubicin, alone, or nanoparticles loaded with doxorubicin on KHOS cells.
FIG. 17B is a graphic representation of the anti-proliferative activity of doxorubicin, alone, or nanoparticles loaded with doxorubicin on $KHOS_{R2}$ cells.
Figures 17C, 17D:
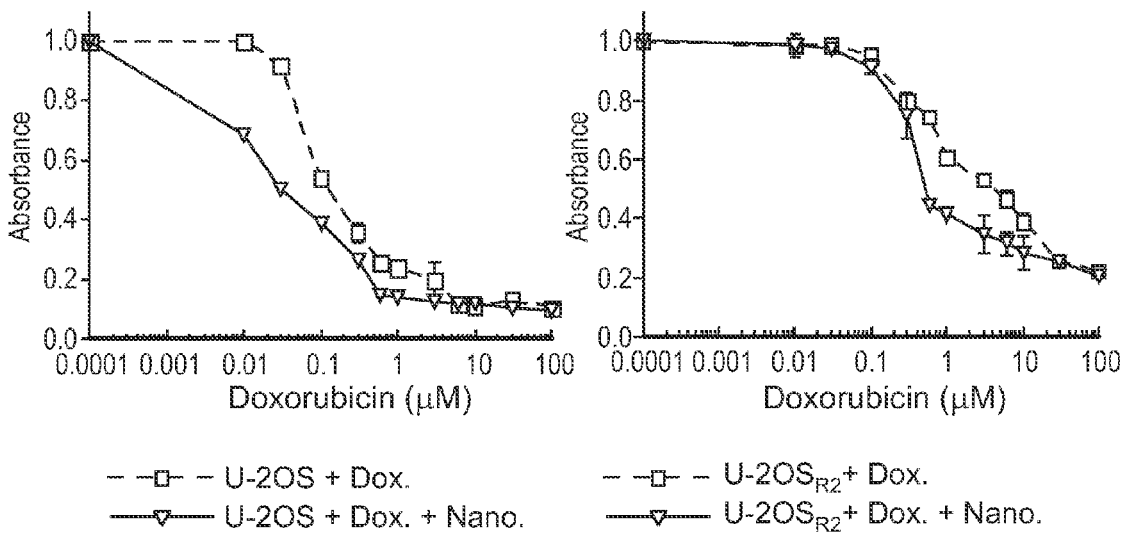
FIG. 17C is a graphic representation of the anti-proliferative activity of doxorubicin, alone, or nanoparticles loaded with doxorubicin on U-2OS cells.
FIG. 17D is a graphic representation of the anti-proliferative activity of doxorubicin, alone, or nanoparticles loaded with doxorubicin on $U-2OS_{R2}$ cells.

Dextran nanoparticle was non-cytotoxic by itself at a dose utilized in this study (FIG. 16). However, nanoparticles loaded with doxorubicin showed an increased amount of anti-proliferative activity in both drug sensitive and resistant osteosarcoma cell lines in a dose dependent manner (FIGS. 20A-D). Nanoparticles loaded with doxorubicin showed 10-fold higher activity compared to doxorubicin, alone, against U-2OS ($IC_{50}$ 0.03 µM to 0.3 µM; FIG. 17C), 5-fold higher activity against $KHOS_{R2}$ ($IC_{50}$ 0.6 µM to $IC_{50}$ 3 µM; FIG. 17B), and 20-fold higher activity against $U-2OS_{R2}$ ($IC_{50}$ 0.3 µM to 6 µM; FIG. 17D).

The effect of nanoparticle on Pgp expression was assessed using Western blot assay. Pgp was not expressed in drug sensitive KHOS and U-2OS, but Pgp was overexpressed in the two drug-resistant cell lines $KHOS_{R2}$ and $U-2OS_{R2}$. The nanoparticle did not suppress the expression of Pgp, but the expression of Pgp gradually increased along with the increase in the concentration of doxorubicin.

Induction of Cellular Apoptosis with Doxorubicin Nanoparticles

Figure 18A:
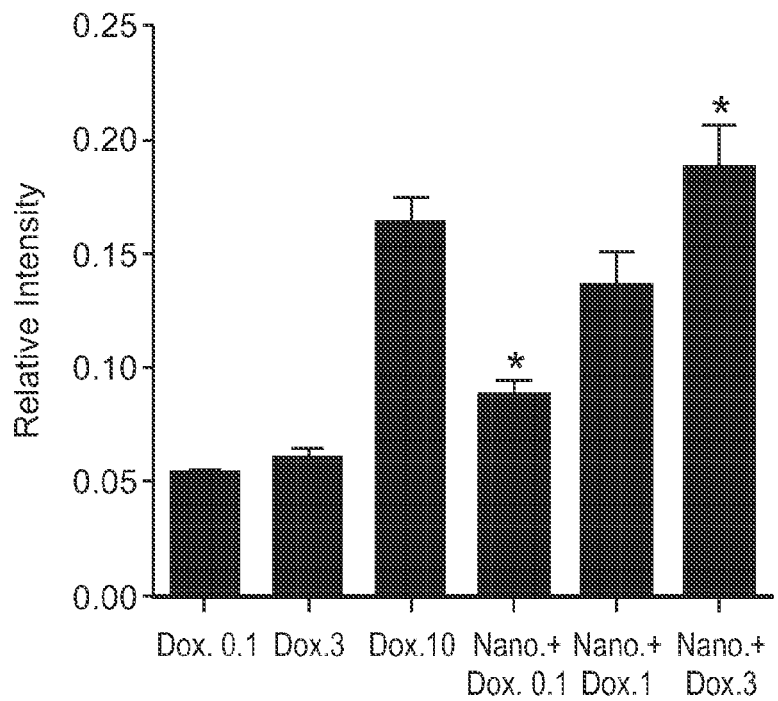
FIG. 18A is a graphic representation of a Western blot analysis of cleavage of PARP for drug sensitive KHOS cells when they were treated with doxorubicin-loaded nanoparticles.
Figure 18B:
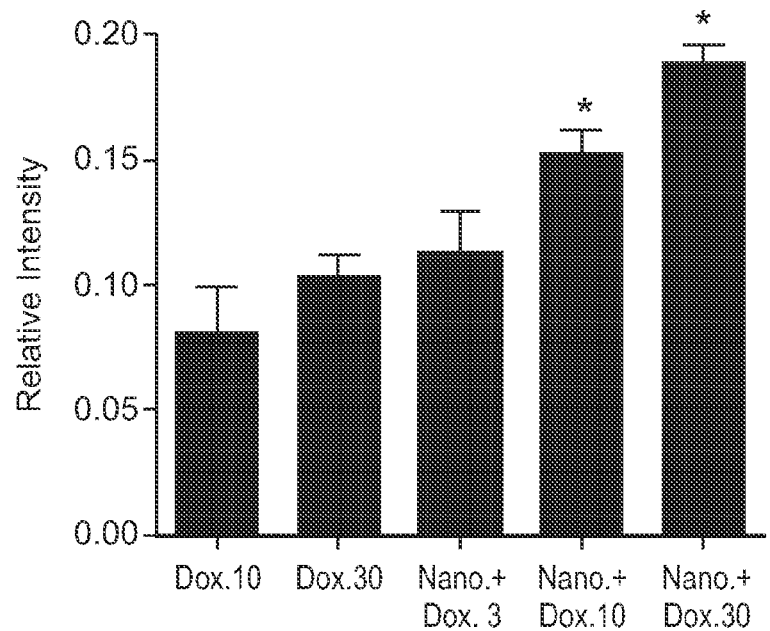
FIG. 18B is a graphic representation of a Western blot analysis of cleavage of PARP for multidrug-resistant $KHOS_{R2}$ osteosarcoma cells when they were treated with doxorubicin-loaded nanoparticles.
Figure 19A:
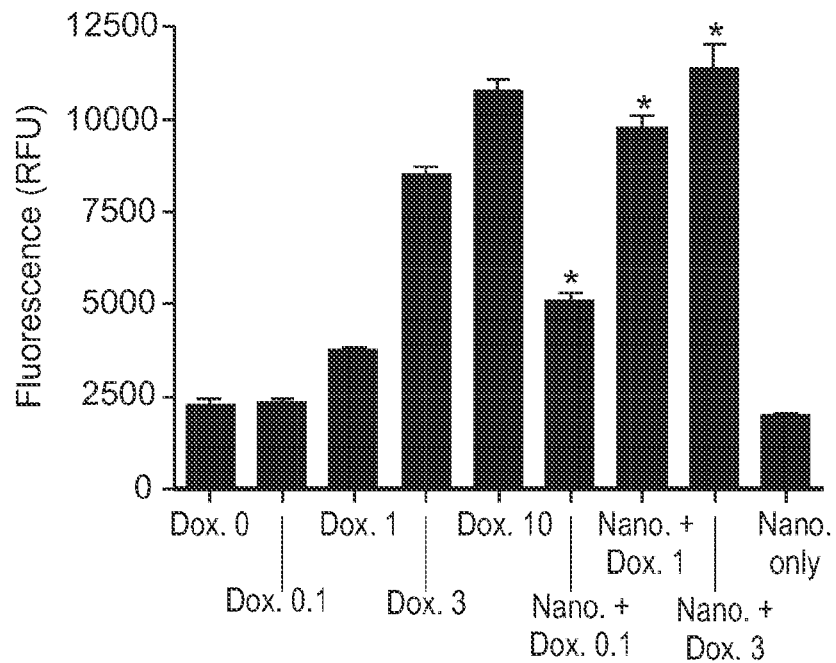
FIG. 19A is a graphic representation of caspase-3/7 activity in KHOS cells treated with doxorubicin-loaded nanoparticles.
Figure 19B:
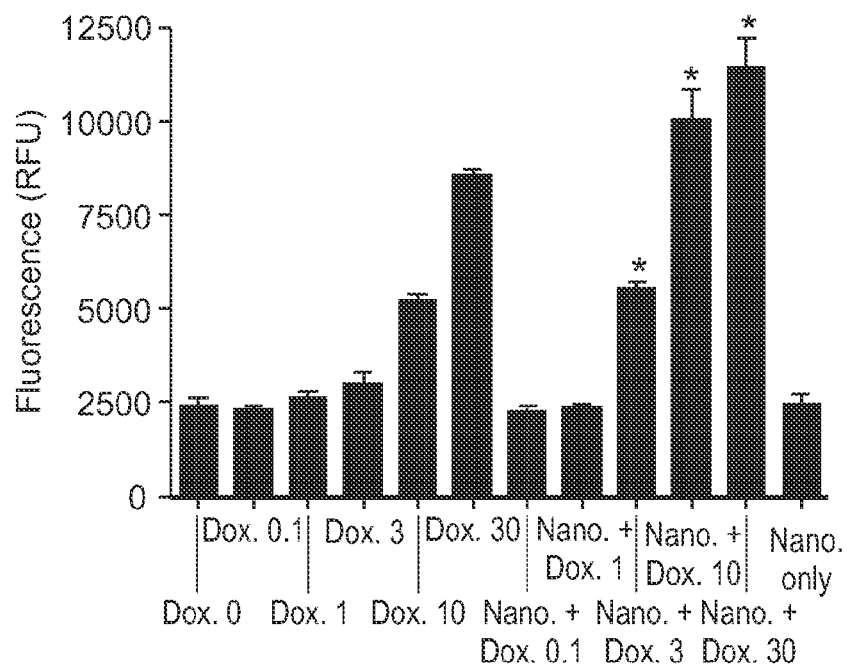
FIG. 19B is a graphic representation of caspase-3/7 activity in $KHOS_{R2}$ cells treated with doxorubicin-loaded nanoparticles.

To assess the efficacy of nanoparticles loaded with doxorubicin to induce apoptosis on KHOS and $KHOS_{R2}$, cleavage of PARP was detected using Western blot assay. The dextran nanoparticle, itself, did not cause cleavage of PARP at a dose utilized in this study. Although higher concentrations of doxorubicin, alone, induced apoptosis, nanoparticles loaded with doxorubicin exhibited a much higher apoptosis induction rate in both drug sensitive (FIG. 18A) and resistant cell lines (FIG. 18B). Further, caspase-3/7 activity was significantly increased when KHOS and $KHOS_{R2}$ were treated with nanoparticles loaded with doxorubicin (FIGS. 19A and 19B).

EQUIVALENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of making a combinatorial formulation library comprising a plurality of therapeutic agent-loaded polymeric nanoparticulate delivery systems, the method comprising:
   a) determining the partition coefficient of a therapeutic agent, wherein the therapeutic agent is selected from an siRNA and an anticancer drug;
      wherein the anticancer drug is selected from the group consisting of tamoxifen, paclitaxel, doxorubicin, camptothecin, topotecan, irinotecan, KRN 5500 (KRN), dexamethasone, methylprednisone, prednisone, prednisolone, ellipticin;
   b) solubilizing the therapeutic agent in an aqueous solution;
   c) combinatorially combining the solubilized therapeutic agent with each of a first plurality of derivatized water-soluble polymers encapsulating the therapeutic agent to form a plurality of nanoparticle cores by self-assembly;
   d) combinatorially combining each of the plurality of nanoparticle cores with each of a second plurality of derivatized water-soluble polymers to form a plurality of hydrogel-encapsulated nanoparticles by self-assembly;

wherein if the therapeutic agent is an siRNA, each of the first plurality of derivatized water-soluble polymers is selected from thiolated dextran derivatives and each of the second plurality of derivatized water-soluble polymers is selected from lipid-modified dextran derivatives;

wherein if the therapeutic agent is an anticancer drug, each of the first plurality of derivatized water-soluble polymers is selected from lipid-modified dextran derivatives and each of the second plurality of derivatized water-soluble polymers is selected from thiolated dextran derivatives; and wherein if the partition coefficient is less than 100, then the lipid-modified dextrans are derived from a fatty acid selected from the group consisting of a $C_2$-$C_{14}$;

wherein if the partition coefficient is greater than 100, then the lipid-modified dextrans are derived from a fatty acid selected from the group consisting of a $C_{14}$-$C_{28}$;

e) combinatorially combining each of the plurality of hydrogel-encapsulated nanoparticles with a plurality of activated PEG derivatives to form a plurality of therapeutic agent-loaded polymeric nanoparticulate delivery systems;

wherein each of the therapeutic agent-loaded polymeric nanoparticulate delivery systems differs from one another by at least one of:
(i) the weight ratio of therapeutic agent to first derivatized water-solubilized polymer to second derivatized water-soluble polymer to activated PEG derivative;
(ii) the identity of at least one of:
(1) the first derivatized water-solubilized polymer;
(2) the second derivatized water-soluble polymer; and
(3) the activated PEG derivative;

thereby making a combinatorial formulation library comprising a plurality of therapeutic agent-loaded polymeric nanoparticulate delivery systems.

2. The method of claim 1, wherein at least a portion of the activated PEG derivatives are modified with thiol groups.

3. The method of claim 1, wherein the therapeutic agent is doxorubicin.

4. The method of claim 1, wherein the library comprises about 2 to about 5,000 different types of nanoparticles.

5. The method of claim 1, wherein the therapeutic agent is an siRNA.

6. The method of claim 1, wherein the therapeutic agent has a partition coefficient less than about 100.

7. The method of claim 1, wherein the therapeutic agent is an anticancer agent selected from the group consisting of doxorubicin, tamoxifen and paclitaxel.

8. The method of claim 1, wherein the therapeutic agent has a partition coefficient greater than about 100.

9. The method of claim 1, wherein the thiolated dextran derivative is derivatized with a functional group selected from the group consisting of cystamine, 2-immunothiolane, cystamine hydrochloride and 2,2'-dithiopyridine.

10. The method of claim 1, wherein the lipid-modified dextran derivative is derivatized with a functional group selected from the group consisting of stearylamine, butylamine, hexylamine, oleylamine, laurylamine, and dodecylamine.

11. The method of claim 9, wherein the thiolated dextran derivative is derivatized with a cystamine functional group.

12. The method of claim 10, wherein the lipid-modified dextran derivative is derivatized with a stearylamine functional group.

13. The method of claim 1, wherein the derivatized water-soluble polymers are cross-linked.

14. The method of claim 1, wherein the mean particle size of the therapeutic agent-loaded polymeric nanoparticulate delivery systems is between about 18.4 and about 430.4 nm.

15. The method of claim 5, wherein the siRNA is selected from the group consisting of EGFP, ABCB1, and MDR1 siRNA.

* * * * *